US009956172B2

(12) United States Patent
McGinity et al.

(10) Patent No.: US 9,956,172 B2
(45) Date of Patent: May 1, 2018

(54) IMPLANT COMPOSITIONS FOR THE UNIDIRECTIONAL DELIVERY OF THERAPEUTIC COMPOUNDS TO THE BRAIN

(71) Applicant: Board of Regents, the University of Texas System, Austin, TX (US)

(72) Inventors: Michael J. McGinity, San Antonio, TX (US); Feng Zhang, Pflugerville, TX (US); John R. Floyd, San Antonio, TX (US); James W. McGinity, Austin, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 0 days. days.

(21) Appl. No.: 15/221,827

(22) Filed: Jul. 28, 2016

(65) Prior Publication Data

US 2017/0027864 A1 Feb. 2, 2017

Related U.S. Application Data

(60) Provisional application No. 62/197,739, filed on Jul. 28, 2015, provisional application No. 62/198,040, filed on Jul. 28, 2015, provisional application No. 62/329,973, filed on Apr. 29, 2016.

(51) Int. Cl.
| | |
|---|---|
| *A61K 31/337* | (2006.01) |
| *A61K 9/00* | (2006.01) |
| *A61K 31/573* | (2006.01) |
| *A61K 31/282* | (2006.01) |
| *A61K 31/495* | (2006.01) |
| *A61K 39/395* | (2006.01) |
| *A61K 31/436* | (2006.01) |
| *A61K 33/24* | (2006.01) |
| *A61K 31/4745* | (2006.01) |
| *A61K 31/40* | (2006.01) |
| *A61K 31/704* | (2006.01) |
| *A61K 31/519* | (2006.01) |
| *A61K 31/155* | (2006.01) |
| *A61K 31/538* | (2006.01) |
| *A61K 31/198* | (2006.01) |
| *A61K 31/661* | (2006.01) |
| *A61K 47/10* | (2017.01) |
| *A61K 47/12* | (2006.01) |
| *A61K 47/14* | (2017.01) |
| *A61K 47/36* | (2006.01) |
| *A61L 27/54* | (2006.01) |

(52) U.S. Cl.
CPC .......... *A61K 9/0085* (2013.01); *A61K 9/0024* (2013.01); *A61K 31/155* (2013.01); *A61K 31/198* (2013.01); *A61K 31/282* (2013.01); *A61K 31/337* (2013.01); *A61K 31/40* (2013.01); *A61K 31/436* (2013.01); *A61K 31/4745* (2013.01); *A61K 31/495* (2013.01); *A61K 31/519* (2013.01); *A61K 31/538* (2013.01); *A61K 31/573* (2013.01); *A61K 31/661* (2013.01); *A61K 31/704* (2013.01); *A61K 33/24* (2013.01); *A61K 39/3955* (2013.01); *A61K 47/10* (2013.01); *A61K 47/12* (2013.01); *A61K 47/14* (2013.01); *A61K 47/36* (2013.01); *A61L 27/54* (2013.01); *A61L 2430/32* (2013.01)

(58) Field of Classification Search
CPC ...... A61K 9/0085; A61K 9/0024; A61L 27/54
See application file for complete search history.

(56) References Cited

U.S. PATENT DOCUMENTS

| | | | |
|---|---|---|---|
| 3,364,200 | A | 1/1968 | Ashton |
| 5,739,169 | A | 4/1998 | Ocain et al. |
| 5,801,005 | A | 9/1998 | Cheever |
| 5,824,311 | A | 10/1998 | Greene |
| 5,830,880 | A | 11/1998 | Sedlacek et al. |
| 5,846,945 | A | 12/1998 | McCormick |
| 6,232,287 | B1 | 5/2001 | Ruoslahti et al. |
| 6,488,963 | B1 | 12/2002 | McGinity |
| 6,528,481 | B1 | 3/2003 | Burg et al. |
| 7,452,964 | B2 | 11/2008 | Pasqualini et al. |
| 7,671,010 | B2 | 3/2010 | Arap et al. |
| 7,781,565 | B2 | 8/2010 | Pasqualini et al. |
| 8,450,278 | B2 | 5/2013 | Staquicini et al. |
| 8,507,445 | B2 | 8/2013 | Arap et al. |
| 8,821,913 | B2 | 9/2014 | Wang |
| 2004/0005647 | A1 | 1/2004 | Denardo et al. |
| 2006/0034925 | A1 | 2/2006 | Au |
| 2006/0115537 | A1 | 6/2006 | Sung et al. |
| 2006/0223114 | A1 | 10/2006 | Stemmer et al. |
| 2006/0234299 | A1 | 10/2006 | Stemmer et al. |
| 2007/0148095 | A1 | 6/2007 | Chen et al. |
| 2012/0141550 | A1 | 6/2012 | Maye et al. |
| 2013/0138032 | A1 | 5/2013 | Kim |
| 2014/0024610 | A1 | 1/2014 | Pisani et al. |

FOREIGN PATENT DOCUMENTS

| | | |
|---|---|---|
| WO | WO 2007/112286 | 10/2007 |
| WO | WO 2008/121949 | 10/2008 |

(Continued)

OTHER PUBLICATIONS

Aburahma and Badr-Eldin, "Compritol 888 ATO: A Multifactional Lipid Excipient in Drug Delivery Systems and Nanopharmaceuticals", *Expert Opinion on Drug Delivery*, 11(12), p. 1865-1883, 2014.

(Continued)

*Primary Examiner* — Kyle A Purdy
(74) *Attorney, Agent, or Firm* — Parker Highlander PLLC

(57) ABSTRACT

The present invention provides, in some aspects, bilayered and trilayered pharmaceutical implant compositions for the unidirectional delivery of anti-cancer compounds to the brain over a period of time (e.g., several weeks, 1, 2, 3, 4, 5, 6, 7 days, or 1, 2, 3, weeks, or any range derivable therein) following the removal of glioblastoma multiforme or other malignant tumors in the brain.

64 Claims, 7 Drawing Sheets

(56) References Cited

FOREIGN PATENT DOCUMENTS

| WO | WO 2011/053435 | 5/2011 |
|---|---|---|
| WO | WO 2014/036290 | 3/2014 |
| WO | WO 2014/087413 | 6/2014 |

OTHER PUBLICATIONS

Carbone et al., "FA-Loaded Lipid Drug Delivery Systems: Preparation, Characterization and Biological Studies", *European Journal Pharmaceutical Sciences*, 14(52) p. 12-20, 2014.

Cho et al., "Therapeutic Nanoparticle for Drug Delivery in Cancer", *Clinical Cancer Research*, 14, p. 1310, 2008.

Forier et al., "Lipid and Polymer Nanoparticles for Drug Delivery to Bacterial Biofilms", *Journal of Controlled Release*, 190, p. 607-623, 2014.

Gabathuler, "Approaches to Transport Therapeutic Drugs Across the Blood-Brain Barrier to Treat Brain Diseases", *Neurobiology of Disease*, 37, p. 48-57, 2010.

International Search Report and Written Opinion issued in International Application No. PCT/US2016/044390, dated Oct. 12, 2016.

Jiang et al., "Novel Anti-glioblastoma Agents and Therapeutic Combinations Identified from a Collection of FDA Approved Drugs", *Journal of Translational Medicine*, 12, 2014.

Kalepu et al., "Oral Lipid-Based Drug Delivery Systems—An Overview", *Acta Pharmaceutica Sinica B*, 3(6), p. 361-372, 2013.

Kreye et al., "Drug release mechanisms of cast lipid implants", *European Journal of Pharmaceutics and Biopharmaceutics*, 78(3): 394-400, 2011.

Kreye et al., "Lipid Implants as Drug Delivery Systems", *Expert Opinion Drug Delivery*, 5(3), p. 291-307, 2008.

Masserini, "Nanoparticles for Brain Drug Delivery", *International Scholarly Research Notices Biochemistry*, 2013, Article ID 238428, 2013.

Menei et al., "Drug Delivery into the Brain Using Poly(lactide-co-glycolide) Microspheres", *Expert Opinion Drug Delivery*, 2(2), 363-376, 2005.

Pardridge, "Drug Delivery to the Brain", *Journal of Cerebral Blood Flow & Metabolism*, 17, p. 713-731, 1997.

Schwab et al., "Studies on the Lipase Induced Degradation of Lipid Based Drug Delivery Systems", *Journal of Controlled Release*, 140, p. 27-33, 2009.

Shapira et al., "Evolving Lipid-Based Delivery Systems in the Management of Neoplastic Disease", *Oncology Reviews*, 113, 2009.

Tiwari et al., "Drug Delivery Systems: An Updated Review", *International Journal of Pharmaceutical Invesitgation*, 2(1), p. 2-11, 2012.

Upadhyay, "Drug Delivery Systems, CNS Protection, and the Blood Brain Barrier", *BioMed Research International*, 2014, Article ID 869269, 2014.

Zara and Nabila, "Optimizing Oral Drug Delivery Using Lipid Based Formulations", *International Research of Pharmacy*, 5(7), 2014.

Zhang et al., "The Effect of Temozolommide/Poly(lactide-co-glycolide) (PLGA)/Nano-Hydroxyapatite Microspheres on Glioma U87 Cells Behavior", *International Journal of Molecular Sciences*, 13(1), p. 1109-1125, 2012.

Zhu et al., "Examination of Aqueous Oxidized Cellulose Dispersions as a Potential Drug Carrier. I. Preparation and Characterization of Oxidized Cellulose-Phenylpropanolamine Complexes", *AAPS PharmSciTech*, 5(4), p. 138-144, 2004.

IMPLANT COMPOSITIONS FOR THE UNIDIRECTIONAL DELIVERY OF THERAPEUTIC COMPOUNDS TO THE BRAIN

This application claims the benefit of U.S. Provisional Patent Application No. 62/197,739, filed Jul. 28, 2015, U.S. Provisional Patent Application No. 62/198,040, filed Jul. 28, 2015, and U.S. Provisional Patent Application No. 62/329,973, filed Apr. 29, 2016, the entirety of which are incorporated herein by reference.

BACKGROUND OF THE INVENTION

1. Field of the Invention

The present invention relates generally to the field of pharmaceutics and medicine. More particularly, it concerns pharmaceutical implants for drug delivery and methods of use thereof.

2. Description of Related Art

There have been many therapeutic methods developed to treat brain cancer, including surgery, radiotherapy and chemotherapy. The present invention relates to pharmaceutical compositions that have activity as anti-cancer agents and to the methods for the treatment of cancer in patients.

Glioblastoma Multiforme is a grade 4 astrocytoma. It is an aggressive cancer that grows from the supportive cells in the brain and is diffusely infiltrative. The current standard treatment is aggressive surgical debulking followed by combined modality therapy of chemotherapy and radiation. Despite the neurosurgeon successfully resecting all visible abnormal tissue during surgery, there are normally many cancer cells that extend well past the resection cavity and are still present in the patient after the surgery. The average survival rate for patients with glioblastoma multiforme who have had aggressive treatments, including surgical resection, radiotherapy and chemotherapy, has been reported to be about fourteen months. It has also been reported that less than 30% of patients survive two years. Long-term survival is extremely rare.

Billions of dollars have been spent over the past 30 years on new therapies with survival benefits only increasing on the scale of months, not years, and presently no curative therapies exist. Outside of standard chemotherapeutics, anti-angiogenics have shown only minimal benefit. Currently, researchers are working on individualized therapy based on specific genetic mutations of a patient's individual tumor. Vaccines are being developed to combat some of these mutations. Local chemotherapy at the tumor resection site has also been attempted with some minimal degree of success. From a scientific standpoint, trials have shown statistically significant survival improvements, but a survival expectation of 15 months rather than 13 months may represent only a very modest improvement for the patient. Although researchers have successfully cured cancer in some animal models, this success has rarely been duplicated in humans with glioblastoma.

A variety of biodegradable polymers, including the polyesters and polyanhydrides have been reported in the literature as carrier polymers for anti-cancer compounds. Of these materials, polylactide-co-glycolic acid (PLGA) has been extensively studied. However, although various biodegradable polymeric materials have been tested for drug delivery, relatively few commercial products that have reached the marketplace utilize either polyesters or polyanhydrides.

One such product that has been marketed is the Gliadel® wafer implant that contains carmustine for the treatment of malignant gliomas. Gliadel® has been on the market for almost twenty years and is the only FDA approved local implant to treat glioblastoma multiforme. There are presently no generic equivalents on the market. The polyanhydride carrier in the Gliadel® implants is a co-polymer, polifeposan, which consists of 1,3-bis(p-carboxyphenoxy) propane and sebacic acid in a molar ratio of 80 to 20. Molecules of active ingredient are distributed through the polymer matrix, which controls drug delivery at the site of the implant. The product is designed to deliver therapeutic levels of the drug that cannot be achieved with other routes of drug delivery, including i.v. and oral. It has been reported that the median survival of patients with Gliadel® wafers for recurrent glioblastoma was thirty-one weeks compared to twenty-three weeks for those on placebo, although this was not statistically significant. Survival benefit was indeed statistically significant in patients with newly diagnosed glioblastoma, although the benefit is deemed as modest by most (~2 months).

The increase in side effects such as seizures, wound healing difficulties, the development of cysts, and reactive brain edema seen with the Gliadel® wafers has been a major concern to neurosurgeons wishing to use this product on their patients. Up to eight wafers can be implanted in a patient following removal of the tumor. There have been reports where some neurosurgeons have re-operated to remove these wafers from patients due to severe adverse side effects.

Several theories have been proposed regarding the reasons for increased side effects and toxicity of the Gliadel® wafers in patients when compared to a placebo. For implants based on the biodegradable polyesters and polyanhydrides, there is a potential for toxicity from dose dumping (burst effect), inconsistent drug release and the breakdown of the polymer from hydrolysis or enzymatic degradation. The by-products of polyanhydride polymer degradation include the formation of carboxylic acids amongst other byproducts. The presence of agents to prevent oxidation of the polymer in the solid state may also contribute to these side effects. Irritation at the cellular level by these low molecular weight degradation compounds may be one of the causes of toxic side effects. Slight variations in the molecular weight of the polymer may also result in higher levels of low molecular weight fractions, which will biodegrade faster than the higher molecular weight fractions in the polymeric carrier. Acidic by-products can also be generated during storage of the polymers, which may influence the long term chemical stability of the biologically active compound. Since these polyanhydrides are soluble in most organic solvents, the incorporation of a therapeutic agent into such polymers generally occurs using an organic solvent which dissolves the polymer and often times the anticancer compound, prior to the evaporation of the solvent to form the finished delivery system. These organic solvents used to dissolve the polymers include dichloromethane, acetone, tetrahydrofuran, and ethyl acetate and residual solvents in these polymeric devices have their own inherent toxicity. Dichloromethane is one of the most popular solvents reported in the literature to prepare films or wafers, microparticles, and microcapsules of drug-containing biodegradable polymeric formulations. The FDA has classified dichloromethane as a Class 2 solvent, which should be limited in pharmaceutical products due to its inherent toxicity. In 2012, the limit for this solvent in a pharmaceutical product was six hundred parts per million. The breakdown or erosion of a polyester or a polyanhydride based delivery system at the site of implantation in the brain or at other sites of the body may cause the formation of particles or agglomerate of polymer that can irritate surrounding tissue, which may result in adverse side effects.

Certain problems exist for current treatments for glioblastoma multiforme. The current standard treatment for patients suffering from glioblastoma multiforme is to begin taking oral temozolomide capsules two to four weeks after surgery. Radiation treatments are usually initiated in a similar timeframe. The delay allows for the wound to begin the healing process. The disadvantage of the delay is that cancer cells continue to grow during this time period.

Temozolamide can also display adverse side effects. Commercial capsules of temozolomide are available in doses ranging from 5 mg to 250 mg. The drug has a short biological half-life of approximately 1½ hours and thus must be frequently administered to patients to maintain therapeutic levels. Multiple side effects have been reported for temozolomide including nausea, vomiting, constipation, headache and fatigue. These side effects occur in greater than 30% of patients taking temozolomide capsules. Other, less common, side effects have also been reported. Various compositions have been generated in an attempt to try to alter the release of temozolamide, such as the tableted microspheres described in U.S. Pat. No. 8,821,913.

Lipids have been studied for applications such as intramuscular implants and excipients in parenterals and oral solid dosage forms; however, major problems have been observed with implants and oral tablets that rely upon lipids to retard drug release, include erratic and incomplete drug release performance. "Tailing", is a phenomenon, where the final 15-25% of the drug remains locked in the wax matrix, resulting in subtherapeutic levels of the drug substance.

Additional efforts to generate delivery systems have also resulted in various challenges. To resolve the erratic release properties and physical stability issues with lipid based systems, numerous researchers have included water soluble pore forming polymers such as polyethylene glycol in the formulation. Hydrophilic polymers have also been studied as retardant carrier excipients in solid dosage forms, including implants. However, the dissolution and swelling properties of these implants would result in high levels of drug being released directly into the brain cavity over a short period of time. For implants that deliver anti-cancer compounds to the cavity of the brain following surgical removal of the tumor, drug release over a period of 1-2 days would be ineffective since therapeutic levels of the drug need to be maintained over periods of weeks, not days. Furthermore, by releasing the drug directly into the fluid of the brain cavity, the concentration would be low resulting in minimal diffusion of the active drug molecules across the surface of the cavity into the brain. In addition, the drug would circulate to other normal portions of the central nervous system, possibly leading to side effects. Clearly, there is a need for improved methods and implants for the treatment of brain tumors.

SUMMARY OF THE INVENTION

The present invention overcomes limitations in the prior art by providing, in some aspects, multilayered implants or wafers that may be used, e.g., to deliver a chemotherapeutic agent and/or a steroid to the brain after the resection of a brain tumor. For example and as noted herein, implants of the present invention can result in a slowed release of a drug from the implant or wafer that may improve the therapeutic effect of the drug; additionally, in some aspects, a hydrophobic coating on the implant may reduce, slow, minimize, or substantially prevent release of the drug into the cerebrospinal fluid in order to improve the therapeutic effect of the drug (e.g., an chemotherapeutic and/or a steroid).

In some aspects of the present invention, an anti-cancer compound is formulated into a multilayered (e.g., bilayered or trilayered) wafer implant that can be delivered directly to the wall of the cavity in the brain from where a tumor was removed, to increase survival rates in cancer patients. The slow release of the drug from the implant can allow for the absorption and distribution of the anti-cancer compound into the local environment of the brain to provide therapeutic levels of the active moiety over extended time periods, e.g., to kill cancer cells in the brain.

The composition of the drug-containing layer of the wafer implant may include or comprise one or more drugs, a lipid and a hydrophilic polymer and, optionally, one or more other additives. The implant may be applied to the inner surface of the resection cavity in the brain following surgical removal of the tumor. A second top layer can comprise one or more hydrophobic agents, which can reduce, prevent, slow, or minimize the diffusion of drug from the implant into the cerebrospinal fluid of the resection cavity. Through this property, this layer may promote unidirectional absorption of drug through the inner wall in the cavity. The two layers are preferably in a side-by-side configuration. An optional third layer may comprise a hydrophilic polymer, e.g., to further enhance bioadhesiveness of the implant to the wall of the resection cavity. When the third layer is used, the drug containing layer of the implant may preferably be sandwiched between the hydrophobic layer and the hydrophilic polymer layer. A hydrophobic coating may be applied to all surfaces of the wafer where drug release is not desirable. In some embodiments, this includes the sides of the wafer and the hydrophobic layer, leaving the bioadhesive layer non-coated and therefore promoting drug release in a substantially unidirectional fashion. Thus, in some embodiments, anti-cancer compounds that are ineffective when administered via a given route of administration (e.g., by the oral or parenteral route) and/or have difficulty in crossing the blood-brain barrier by the traditional routes of administration may nonetheless be administered to the brain. For example, various anti-cancer agents that are toxic when administered (e.g., systemically or orally) may be administered to a subject in an implant of the present invention to achieve therapeutic concentrations in the brain. High temperature curing of these implant compositions may be employed to increase the adhesion of both the hydrophobic and hydrophilic layers to the drug containing layer.

It has been found in various aspects of the present invention that biocompatible pharmaceutical wafer implant compositions comprising biologically active compounds to treat tumors (e.g., malignant tumors) can be prepared using lipids as inert carrier materials and hydrophilic water soluble pore forming polymeric agents to regulate the drug release rate. The wafers may optionally include one or more additives (e.g., to improve processing and to control the rate of release of the active agent from the solid dosage form; or a preservative, antibiotic, or antimicrobial agent to reduce microbial growth and/or infection). This combination of ingredients in the wafer or implant may provide for a controlled release of the anti-cancer compound(s) at the tumor site, while causing little or no change in the pH at the site of implantation. Thus, in some embodiments, the wafer or implant results in essentially no harmful release of byproducts to irritate the cellular linings of the surrounding tissues.

In one aspect, the present invention relates to a biocompatible drug delivery implant for positioning adjacent to a biological tissue for delivering one or more drugs thereto, the implant comprising at least two layers, a drug-containing layer having a drug elution surface to be positioned proximal to the tissue, and, a further layer or layers comprising a lipophilic backing layer and/or a hydrophobic coating, said further layer or layers being positioned distal to the drug elution surface, wherein: a) the drug-containing layer comprises one or more drugs, a hydrophilic polymer or pore forming agent, and a biocompatible hydrophobic lipid or polymer; b) the lipophilic backing layer comprises a biocompatible hydrophobic lipid or polymer; and c) the hydrophobic coating comprises a biocompatible hydrophobic lipid or polymer and coats surfaces of the implant that are not to be positioned proximal to the tissue and; and further, when each of layers a), b) and c) are present, the lipophilic backing layer is positioned between the drug-containing layer and the hydrophobic coating. In some embodiments, the implant comprises layers a) and b). In some embodiments, the implant comprises layers a) and c). In some embodiments, the implant comprises layers a), b) and c). The implant may further comprise a drug-permeable, hydrophilic layer d) positioned between the drug elution surface of the drug-containing layer and to be positioned proximal to the tissue. In some embodiments, the layer d) does not contain the drug. The layer d) may contain a steroid. In some embodiments, the layer d) contains the drug. In some embodiments, the layer d) contains a steroid and the drug. In some embodiments, the steroid is dexamethasone. In some embodiments, the hydrophobic lipid or polymer in layers a), b), and/or c) is a steroid or a fatty acid. The steroid may be a cholesterol. In some embodiments, the fatty acid is a saturated fatty acid. The saturated fatty acid may have 6 to 24 carbon atoms or 12 to 24 carbon atoms. The fatty acid may be stearic acid, palmitic acid, or a glyceride. In some embodiments, the glyceride contains a mixture of monoglyceride, diglyceride, and triglyceride. In some embodiments, the mixture contains predominately diglyceride. The glyceride may be a glyceryl behenate or stearin (tristearin). In some embodiments, the hydrophobic lipid is glycerol behenate, a fatty acid, a cholesterol, a glyceride, a hydrogenated vegetable oil, tristearin, or the like. In some embodiments, the hydrophilic polymer present in layer a) and/or d) is a polyether or a polysaccharide. In some embodiments, the hydrophilic polymer is a polyethylene oxide, polypropylene oxide, or a polyethylene glycol. In some embodiments, the hydrophilic polymer is a polyethylene oxide or a polysaccharide. In some embodiments, the polysaccharide is chitosan or polyanhydroglucuronic acid. The hydrophilic polymer may comprise a mixture of a polyether and a polysaccharide. In some embodiments, the hydrophilic polymer is a mixture comprising polyethylene oxide and chitosan. The hydrophilic polymer may be polyethylene oxide or polyanhydroglucuronic acid. In some embodiments, the hydrophilic polymer is polyethylene oxide, chitosan, povidone (PVP or polyvinylpyrrolidone), or polyanhydroglucuronic acid. The drug may be an anti-cancer compound. The anti-cancer compound may be a chemotherapy or a chemotherapeutic agent. In some embodiments, the chemotherapeutic is temozolomide, paclitaxel, cetuximab, irinotecan, everolimus, carboplatin, or docetaxel. The drug may be cisplatin, topotecan, bevacizumab, doxorubicin, everolimus, paclitaxel, irinotecan, carboplatin, D-actinomycin, docetaxel, pitavastatin, methotrexate, temozolomide, epirubicin, cetuximab, a copper chelating agent, carmustine, a synthetic alkyl lysophospholipid, a bioactive sulfated saponin, steroid, or a statin. In some embodiments, the drug is a steroid. In some embodiments, layer a) comprises both a chemotherapeutic agent and a steroid. In some embodiments, layer a) comprises a chemotherapeutic agent, and wherein the implant further comprises the layer d), wherein layer d) comprises a steroid. Layer a) may further comprise a steroid. The steroid may be dexamethasone or dexamethasone sodium phosphate. In some embodiments, the chemotherapeutic agent is temozolomide or paclitaxel; and wherein the steroid is dexamethasone. In some embodiments, the implant is substantially circular or elliptical in shape. In some embodiments, the implant is further defined as a wafer. The wafer or tablet may be configured for insertion into a resection cavity. The implant or wafer may further comprise an additional therapeutic agent (e.g., an antibiotic, an antimicrobial agent, a statin, an anti-fungal agent, an anti-viral agent, a steroid, an anesthetic, a local anesthetic, or a NSAID). In some embodiments, the additional therapeutic agent is an antibiotic or an antimicrobial agent. In some embodiments, the implant does not contain an organic solvent. In some embodiments, the implant contains an organic solvent, or no more than a trace amount or a residual amount of the organic solvent. The organic solvent may be ethanol, dichloromethane, acetone, tetrahydrofuran, or ethyl acetate.

In some embodiments, the drug-containing layer comprises 1, 2, 3, or all of glyceryl behenate, stearic acid, polyanhydroglucuronic acid, and/or polyethylene oxide. The lipophilic backing layer and/or the hydrophobic coating may comprise 1, 2, or all of stearic acid, glyceryl behenate, and/or chitosan. In some embodiments, the lipophilic backing layer and the hydrophobic coating are made of the same or essentially the same compounds or mixture of compounds. In some embodiments, the lipophilic backing layer and the hydrophobic coating together form a substantially homogenous hydrophobic layer. In some embodiments, the lipophilic backing layer and the hydrophobic coating comprise different compounds. The hydrophobic coating may consist of or consist essentially of glyceryl behenate. In some embodiments, the hydrophobic coating comprises glyceryl behenate in combination with 1, 2, 3, or all of stearic acid, palmitic acid, cholesterol, and/or chitosan. In some embodiments, the drug-containing layer comprises glyceryl behenate and/or stearic acid, in combination with polyanhydroglucuronic acid and/or polyethylene oxide. The drug-containing layer may comprises glyceryl behenate, stearic acid, and polyethylene oxide. The drug-containing layer may further comprises lipase, cholesterol, glyceryl tristearate, and/or poloxamer F-68. In some embodiments, layer c) and/or layer b) contain lipase. The drug-containing layer may comprise polyethylene oxide or polyanhydroglucoronic acid. The drug-containing layer may comprise polyethylene oxide, glycerol behenate, and/or cholesterol. The drug-containing layer may comprise 1, 2, 3, 4, 5, 6, 7, or all of stearic acid, lipase, cholesterol, glycerol behenate, glyceryl tristearate, poloxamer F-68, and/or polyanhydroglucuronic acid. The hydrophilic polymer may be a polyethylene oxide, a polysaccharide, a protein, an oxidized cellulose polymer, polyanhydroglucuronic acid, a poloxomer, chitosan, or providone (PVP). In some embodiments, the implant further comprises lipase. The implant is configured for insertion into a resection cavity. In some embodiments, the implant has been cured at temperatures of at least about 40° C., 45° C., 50° C., 55° C., 60° C., 65° C., 70° C., 75° C., 80° C., 85° C., 90° C., 95° C., 100° C., or up to 200° C. In some embodiments, the implant has been sterilized by gamma radiation, ethylene oxide, or electron beam radiation. In some embodiments, the implant or wafer has been processed by compression, hot-melt extrusion, injection molding, dry powder coating, dipping, coating, spraying, hot-melt granulation, casting, an evaporation technology, or any combination thereof. The implant may comprise: 0.1-50% of the drug, 5-95% of the hydrophobic lipid or polymer, and about 3-50% of the hydrophilic polymer or pore forming agent. In some embodiments, the implant is further defined as a bilayered implant or wafer, or a trilayered implant or wafer. In some embodiments, the implant allows for release of the drug over a period of at least 3, 4, 5, 6, 7, 8, 9, 10, 11, 12, 13, 14, 15, 16, 17, 18, 19, 20, 21, 22, 23, 24, 25, 26, 27, 28, 29, or 30 or more days, or at least 1, 2, 3, 4, 5, or 6 weeks, or any range derivable therein. The implant may further comprise a surfactant, a carbohydrate, a polyol, a protein, a peptide, and/or an excipient.

Another aspect of the present invention relates to a method of treating a disease or traumatic injury in a mammalian subject, comprising administering into a resection cavity in the subject the implant of the present invention or an described above, wherein the drug elution surface is positioned proximal to the resection cavity, and, the further layer or layers comprising the lipophilic backing layer and/or the hydrophobic coating are positioned distal and/or lateral to the drug elution surface. The subject may be a mammal such as, e.g., a human. The resection cavity may be in the brain of the subject. The resection cavity may be in the spine, lung, neck, knee, back, a joint, bladder, or uterus. The disease may be an inflammatory disease, pain, an infection, or inflammation. In some embodiments, the disease is a cancer. The method may further comprise removing part or all of a tumor from the subject via the resection cavity. In some embodiments, the tumor is cancerous. In some embodiments, the tumor is a brain tumor, a glioblastoma or glioblastoma multiforme, or a high grade intrinsic brain tumor. The cancer may be a metastatic cancer. In some embodiments, the surface of the resection cavity or at least of the part the resection cavity is filled with a surgical glue or a fibrin glue, e.g., after wafer implantation. In some embodiments, the resection cavity is filled with surgical glue e.g., after wafer implantation. The surgical glue may be, e.g., DuraSeal®, Tiseal® or Eviseal®, or other similar surgical glue. In some embodiments, part of all of the implant is covered with a biocompatible, biodegradable surgical fabric or Surgicel®.

Some aspects of the present invention may be understood as a method of treating a cancer in a mammalian subject, comprising administering into a resection cavity in the subject a pharmaceutically acceptable implant or wafer, wherein the implant or wafer comprises: (i) a first composition comprising an anti-cancer compound, a lipid, and a hydrophilic polymer; and (ii) a second composition comprising a hydrophobic agent; wherein the second composition is located above or distal to the first composition in the resection cavity.

The method may further comprise administering a third composition into the resection cavity, wherein the third composition comprises a hydrophilic polymer. The third composition may also enhance the bioadhesiveness of the first composition or the second composition. In some embodiments, first composition, the second composition, and any third composition are further defined as pharmaceutical compositions and comprise an excipient. The first composition may be formulated in the resection cavity between the second composition and the third composition.

The anti-cancer compound may be a chemotherapy or a chemotherapeutic agent such as temozolomide, paclitaxel, cetuximab, irinotecan, everolimus, carboplatin, or docetaxel. The first composition may comprise at least a first chemotherapeutic agent and a second chemotherapeutic agent such as a combination of carboplatin and docetaxel.

The hydrophobic agent may be a steroid such as cholesterol. In other embodiments, the hydrophobic agent is a fatty acid such as a saturated fatty acid. The fatty acid may have 6 to 24 carbon atoms or 12 to 24 carbon atoms. A non-limiting example of the fatty acid is stearic acid. In other embodiments, the hydrophobic agent is a glyceride such as a mixture of monoglyceride, diglyceride, and triglyceride. The glyceride mixture may predominately contain one or more diglycerides. In some embodiments, the glyceride is a glyceryl behenate. The first composition may comprise glyceryl behenate, stearic acid, polyanhydroglucuronic acid, and/or polyethylene oxide. The second composition may comprise polyethylene oxide, glycerol behenate, and/or cholesterol. The third composition may comprise stearic acid or glyceryl behenate and/or chitosan.

In some embodiments, the subject is a human. The methods may further comprise removing part or all of a tumor from the subject via the resection cavity. In some embodiments, the tumor is cancerous. The tumor may be a brain tumor such as a glioblastoma or glioblastoma multiforme. In some embodiments, the cancer is a metastatic cancer.

The first layer may comprise temozolomide, stearic acid, lipase, cholesterol, glycerol behenate, poloxamer F-68, and/or polyanhydroglucuronic. The first composition, the second composition, and optionally the third composition may be comprised in a wafer or a tablet. The wafer or tablet may be configured for insertion into the resection cavity. In some embodiments, the wafer or tablet further comprises an antibiotic or an antimicrobial agent. In some embodiments, the wafer or tablet does not contain dichloromethane (methylene chloride), acetone, tetrahydrofuran, or ethyl acetate. The wafer or tablet may not contain an organic solvent.

The implant or wafer may further comprise an additional therapeutic agent such as an antibiotic, a statin, an antifungal agent, an anti-viral agent, an anti-coagulant, a pain medication, an NSAID, or a steroid. The anti-cancer compound may be cisplatin, topotecan, bevacizumab, doxorubicin, everolimus, paclitaxel, irinotecan, carboplatin, D-actinomycin, docetaxel, pitavastatin, methotrexate, temozolomide, epirubicin, cetuximab, a copper chelating agent, carmustine, a synthetic alkyl lysophospholipid, a bioactive sulfated saponin, or a statin. The lipid used herein may be glycerol behenate, a fatty acid, a cholesterol, a glyceride, a hydrogenated vegetable oil, or tristearin.

The hydrophilic polymer may be polyethylene oxide, chitosan, povidone (PVP), or polyanhydroglucuronic acid. The hydrophilic polymer may be a polyether such as a polyethylene oxide or polypropylene oxide. In some embodiments, the hydrophilic polymer is a polyethylene oxide. The hydrophilic polymer may be a polysaccharide such as chitosan. In other embodiments, the hydrophilic polymer comprises a mixture of a polyether and a polysaccharide such as a mixture of polyethylene oxide and chitosan. The hydrophilic polymer may be a polyethylene oxide, a polysaccharide, a protein, an oxidized cellulose polymer, polyanhydroglucuronic acid, a poloxomer, chitosan, or providone (PVP). The implant or wafer may also further comprise a lipase. In some aspects, the surface of the resection cavity or at least of the part the resection cavity is filled with a surgical glue. In some embodiments, the surgical glue is DuraSeal®, Tiseal® or Eviseal®.

Also contemplated are implant or wafer as described in the above methods. The implant or wafer may be pharmacologically acceptable and configured for insertion into a resection cavity. The implant or wafer may be cured at temperatures of at least about 40° C., 45° C., 50° C., 55° C., 60° C., 65° C., 70° C., 75° C., 80° C., 85° C., 90° C., 95° C., 100° C., or up to 200° C. The implant or wafer may also be processed by compression, hot-melt extrusion, injection molding, dry powder coating, hot-melt granulation, casting, evaporation technologies, dipping, spraying, or any combination thereof. In some embodiments, the implant or wafer further comprises an excipient.

In yet another aspect, the present disclosure includes pharmaceutical bilayered wafer implant composition comprising: a. one or more biologically active anti-cancer compounds to treat malignant tumors present in the brain; b. one or more lipid components; c. one or more water soluble hydrophilic pore forming polymeric components; d. optionally one or more other inactive pharmaceutical ingredients; e. a hydrophobic second layer, located side-by-side with the drug containing layer; f bilayered compositions are then cured at elevated temperatures.

The compositions may contain one or more lipid components in the drug layer, including: glycerol behenate, mono, di- and tri-glycerides, long chain fatty acids, cholesterols, and the like. In some embodiments, the compositions comprise 0.1-50% biologically active compounds, 20-95% lipid component, about 5-50% hydrophilic bioadhesive component and 0-50% suitable additives to enhance processing of the wafer or to control the release of the active compound from the implant. The pharmaceutical wafer implant or tablets composition may contain a biologically active compound in sufficient concentrations to achieve a therapeutic level of the compound in a patient over a period of about one week up to about six months. These biologically active compounds may include drugs to treat glioblastoma multiforme. In other embodiments, the biologically active compounds may include drugs to treat a brain tumor such as a high grade intrinsic brain tumor.

In some embodiments, the biologically active compounds can compounds alone or in combination to treat and/or cure malignant brain tumors to include cisplatin, topotecan, bevacizumab, doxorubicin, everolimus, paclitaxel, irinotecan, carboplatin, D-actinomycin, docetaxel, pitavastatin, methotrexate, temozolomide, epirubicin, cetuximab, copper chelating agents, carmustine, synthetic alkyl lysophospholipids, bioactive sulfated saponins statins and the like. The pharmaceutical solid dosage compositions may release the biologically active compound in the brain over a period of about one week up to six months. Similarly, the compositions may further comprise one or more hydrophilic polymers comprising polyethylene (oxide), chitosans, poloxymers, polysaccharides, polyols, proteins, polyanhydroglucuronic acid, peptides, providone (PVP) and the like. In some embodiments, the compositions comprise one or more hydrophilic nonpolymer components comprising amino acids. The compositions may also comprise one or more inert excipients including surfactants, carbohydrates, polyols, proteins, and/or other excipients having no significant effect on the pH of surrounding biological fluid at the site of implantation of the wafer in the brain.

In another aspect, the process of preparing bilayered solid dosage compositions for timed release biologically active anti-cancer compounds to treat and cure malignant tumors comprising in one layer:
  a. one or more biologically active compounds;
  b. one or more lipid components;
  c. one or more hydrophilic polymeric components;
  d. optionally one or more other pharmaceutical inactive ingredients; and
  e. a hydrophobic second layer.

The process may also be performed such that it does not require an organic solvent. In some embodiments, the process comprises using a hot-melt extrusion, compression, injection molding, evaporation, hot-melt granulation, dry powder coating or the like. In some embodiments, the process comprises preparing a pharmaceutical composition implant by:
  a. dissolve or disperse the anti-cancer compound in molten liquid carrier;
  b. disperse or dissolve the hydrophilic polymers in the molten composition;
  c. pour the molten mix into molds to form the implant; and
  d. cool into wafers; or
  e. alternatively, cool, form granules pass through 60 mesh screen, compress into wafers or tablets and, cure at elevated temperature for several hours.

The process may further relate to preparing tablet implant compositions by compression. The process may further comprise process to prepare compositions that will have no significant influence on the pH of the surrounding biological fluid following surgical removal of the malignant tumor. The processes relate to the addition to the anti-cancer compound present in the solid pharmaceutical implant compositions to also include antibiotics, antifungal agents, local anesthetics, NSAIDS, statins, steroids, contraceptives, antivirals, and anti-cancer agents that do cross the blood-brain barrier. In some embodiments, the patient is a mammal such as a mammal.

In some embodiments, the composition may be sterilized by ethylene oxide, gamma radiation, or electron beam radiation. The composition may further a lipase. The compositions may also further comprise a poorly water soluble or water insoluble hydrophobic second layer applied to one surface of the drug containing tablet or wafer. In some embodiments, the compositions may be implanted into a patient's brain, immediately following the surgical removal of the tumor. The composition may be used to provide unidirectional delivery of chemotherapeutic agents to the brain. The compositions may also be applied directly to the wall of the cavity in the brain following surgical removal of the tumor. The compositions may also be applied directly to the wall of the resection cavity in the brain followed by covering with Surgicel® knitted fabric, and/or Duraseal®, Evicel®, or Tisseel® following the surgical removal of the tumor. In one embodiment, the resection cavity is filled with surgical glue. In some embodiments, the compositions also comprise a separate third layer comprising one or more hydrophilic polymers where the final composition comprises a drug containing layer sandwiched between the hydrophobic layer and a hydrophilic polymeric layer.

In some aspects, an implant or wafer of the present invention may comprise temozolomide or other anti-cancer compound(s). The implant or wafer comprising temozolomide or other anti-cancer compounds may be inserted into the resection cavity during the same surgical procedure and/or immediately after the tumor is removed. In some embodiments, an added advantage of the implant wafers provided in the present invention is that the patient begins their chemotherapy at the time of surgery. The bioadhesive hydrophilic components in the implant may facilitate the surgeon applying the device to the wall of the cavity, which can promote drug diffusion into the brain and not the resection cavity fluid. The addition of a second hydrophobic layer to the top surface and/or a coating to desired non-drug eluding sides of the implant can promote unidirectional drug absorption into the tissue and decrease the release of drug into the spinal fluid present in the brain cavity. In contrast to methods of oral administration of temozolomide after a surgery (e.g., to remove a glioblastoma multiforme tumor) involving a delay between the surgery and initiation of the temozolomide therapy, the use of an implant or wafer comprising the temozolomide or another anti-cancer compounds may reduce, minimize, or effectively eliminate the delay between removal of the tumor and initiation of the additional therapy. In some embodiments, utilizing local delivery of the anti-cancer compounds by using implants in the brain, the systemic dose of this agent, when delivered orally, may be reduced, which may also decrease the incidence of known systemic side effects.

In some embodiments, a wafer or tablet of the present invention does not include organic solvents such as a polar aprotic or polar protic solvents. Some non-limiting examples of organic solvents include alcohols, haloalkanes, ketones, esters, and ethers of 12 or less carbon atoms such as ethanol, dichloromethane (or methylene chloride), acetone, tetrahydrofuran, or ethyl acetate. In some embodiments, a wafer or tablet of the present invention may also not include any of the water insoluble polymers that are described in the U.S. Pat. No. 8,821,913.

"Unidirectional" as used herein refers to the diffusion of a therapeutic compound (e.g., anti-cancer compound, chemotherapeutic compound, etc.) out of an implant or wafer of the present invention. A "backing" layer and/or hydrophilic coating containing a hydrophobic material may reduce, minimize, or prevent the therapeutic compound from travelling through a resection cavity towards the exterior surface of a subject (e.g., towards the skull or scalp of a human patient).

In some aspects, the implants or wafers use a hydrophobic agent that is layered distal to or onto the surface of the drug containing layer to promote unidirectional absorption through the wall of the cavity in the brain, following tumor removal. The presence of an optional third hydrophilic layer added to the implant may promote adhesion of the implant directly to the brain along the sides of the resection cavity. The drug containing layer would be "sandwiched" between the hydrophobic and adhesive layer. To further promote the unidirectional flow of the chemotherapeutic agent through the wall of the brain cavity, the implants of the present invention may preferably be held in place with a covering of Surgicel®, a surgical knitted fabric, or a surgical glue such as DuraSeal®, Tiseal® or Eviseal®. The surgical glue applied to the hydrophobic layer of the implant, may harden within seconds and may not only maintain adherence of the implant to the wall of the brain cavity, but may also help prevent drug release from the sides of the implant into the brain cavity, thereby promoting the unidirectional absorption of drug from the implant into the local environment of the brain.

The hydrophilic polymers present in the drug containing layer of the implant may influence both the erosion and permeability of the implant. The curing of the wafer at elevated temperature can increase the adhesion amongst layers in the implant. Preferred hydrophilic polymers include polyethylene oxide, chitosan, povidone (PVP) and polyanhydroglucuronic acid. The lipids may be slowly broken down by enzymes in the lipase family, which are normally found throughout the human body. Additional added low doses of lipase in the dosage form may also control the release rate of the active compound from the dosage form. Lipase levels in the blood serum have been reported to increase after surgery but then decline sharply, particularly in the brain. In some embodiments, about 1.5-4%, 1, 1.5, 2, 2.5, 3, 3.5, 4, 4.5, or 5% or any range derivable therein of polyethylene oxide may be particularly useful in implants or wafers of the present invention.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1:
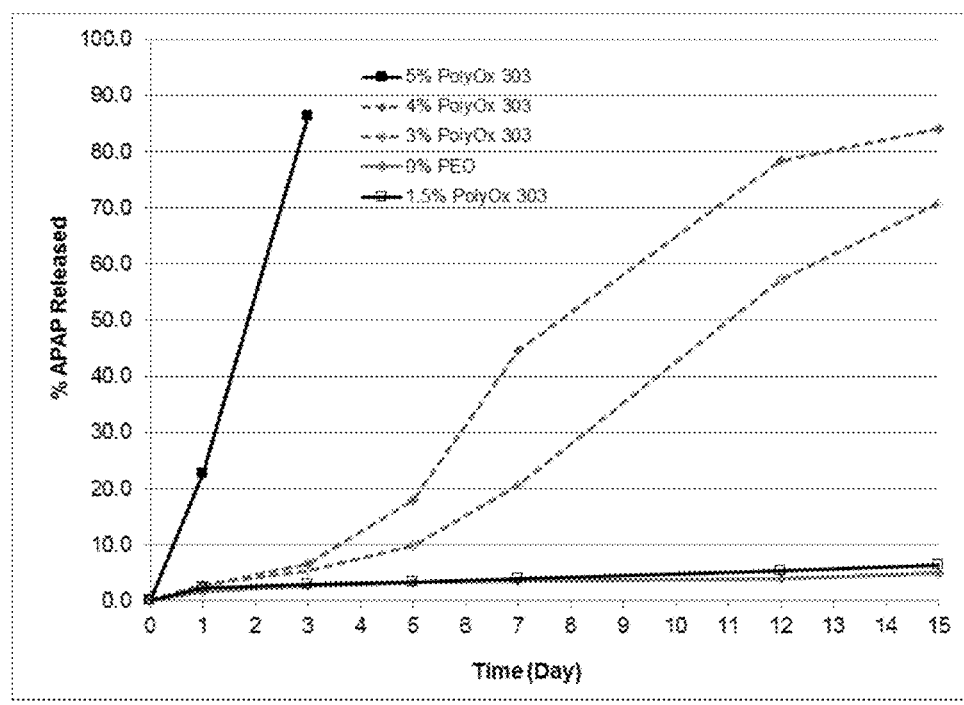
FIG. 1: Release from single layer wafers. Each of the single layer wafers were tested with different PolyOx 303 (solid line and solid diamond, 0% PolyOx 303; solid line and open square, 1.5% PolyOx 303; dashed line and open diamond, 3% PolyOx 303; dashed lines and solid diamond, 4% PolyOx 303; and solid line and solid square, 5% PolyOx 303)
Figure 2:
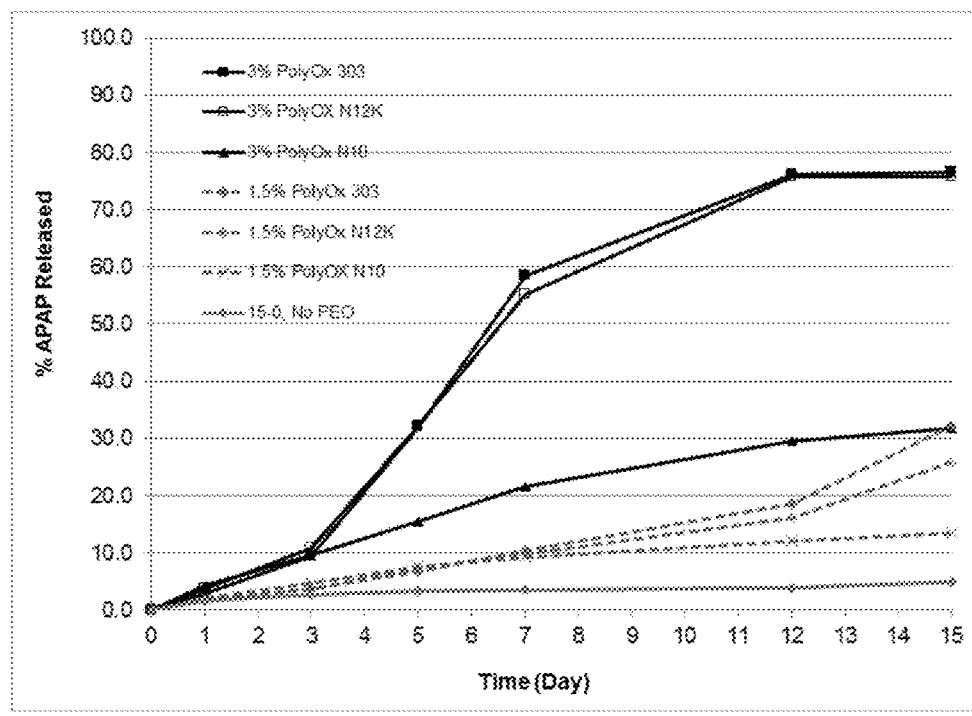
FIG. 2: Release from coated bilayer wafers with different grades of PEO and different levels (0-3%) of PEO. (solid line and solid diamond, No PEO; dashed line and solid cross, 1.5% PolyOx N10; dashed line and open diamond, 1.5% PolyOx N12K, dashed line and solid diamond, 1.5% PolyOx 303; solid line and solid diamond, 3% PolyOx N10; solid line and open square, 3% PolyOx N12K; and solid line and solid square, 3% PolyOx 303). Release of acetaminophen (APAP) from coated bi-layer (bio-adhesive layer and drug layer) wafer was measured. The drug layer composition included 5% APAP, the above noted percent of PEO of various grades, and glycerol behenate q.s. to 100%, a total of 200 mg including a bio-adhesive layer of 50 mg PEO 303. These compositions were used to investigate the percent of PEO and grade of PEO on drug release from coated bi-layer wafer. Without the hydrophobic backing layer, portion of drug layer melted away during dip-coating process. As a result, only 75% drug was recovered at the end of the drug release testing. As a result of these data, it may be concluded that the higher the PEO molar mass, the faster the drug release is and the higher the percent of PEO, the faster the drug release is.
Figure 3:
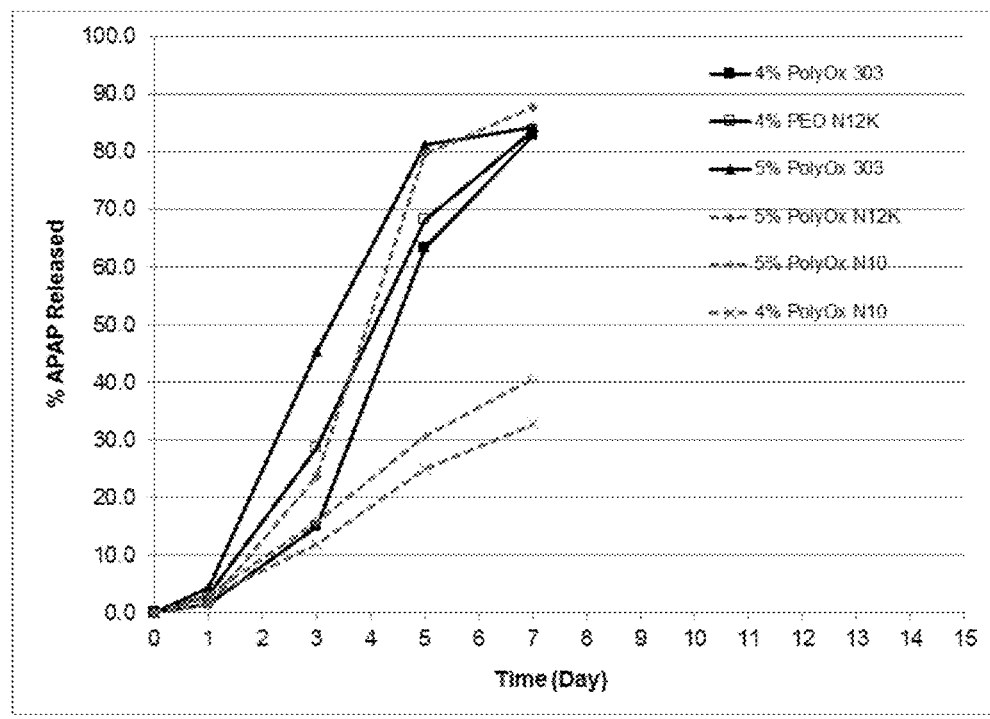
FIG. 3: Release from coated bilayers with different grades and levels (4-5%) of PEO. (dashed line and solid cross, 4% PolyOx N10; solid line and open square, 4% PolyOx N12K, solid line and solid square, 4% PolyOx 303; dashed line and open diamond, 5% PolyOx N10; dashed line and solid diamond, 5% PolyOx N12K; and solid line and solid diamond, 5% PolyOx 303).
Figure 4:
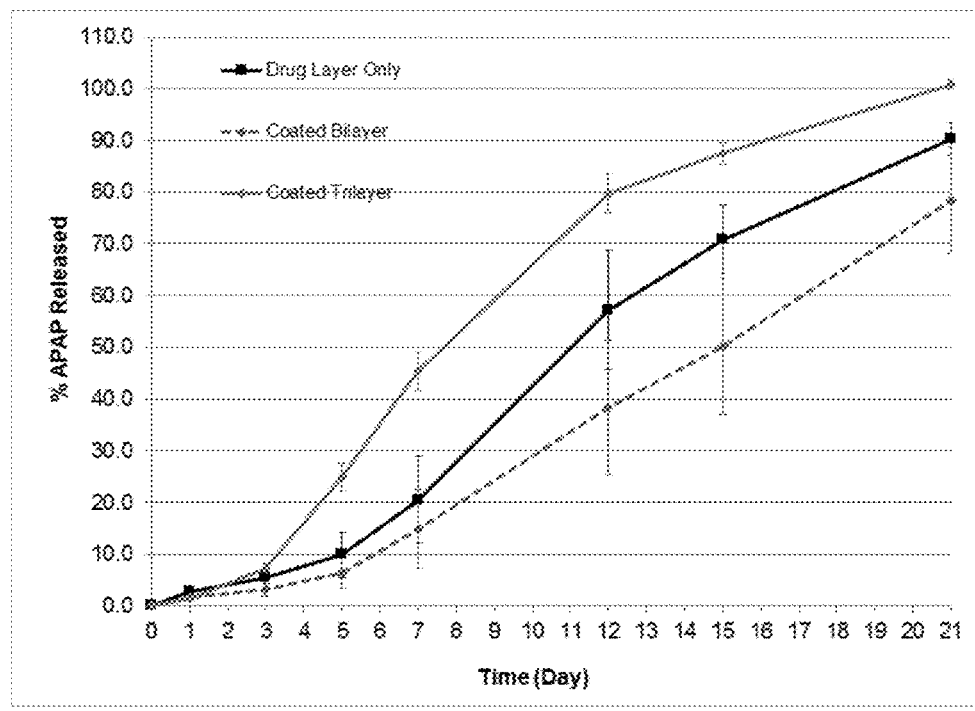
FIG. 4: Release from single layered, bi-layer, and tri-layered wafers. Release of acetaminophen (APAP) from single (drug layer), bi-layer (drug layer+hydrophobic layer) and tri-layer (bio-adhesive layer, drug layer, hydrophobic layer and coating) wafer. The composition of the wafer includes: (1) Drug layer composition: 5% APAP, 3% PEO 303, and 92% glycerol behenate, (2) Hydrophobic layer: 100 mg glycerol behenate, and (3) Bioadhesive layer: 50 mg PolyOx 303. The effect of the coating and bioadehsive layer on APAP release was analyzed. As can be seen in the figure, the coating slowed down drug release by reducing the total surface area available for drug release. Without wishing to be bound by any theory, the presence of bio-adhesive layer accelerated drug release may be based upon increased facilitation the hydration of drug layer.
Figure 5:
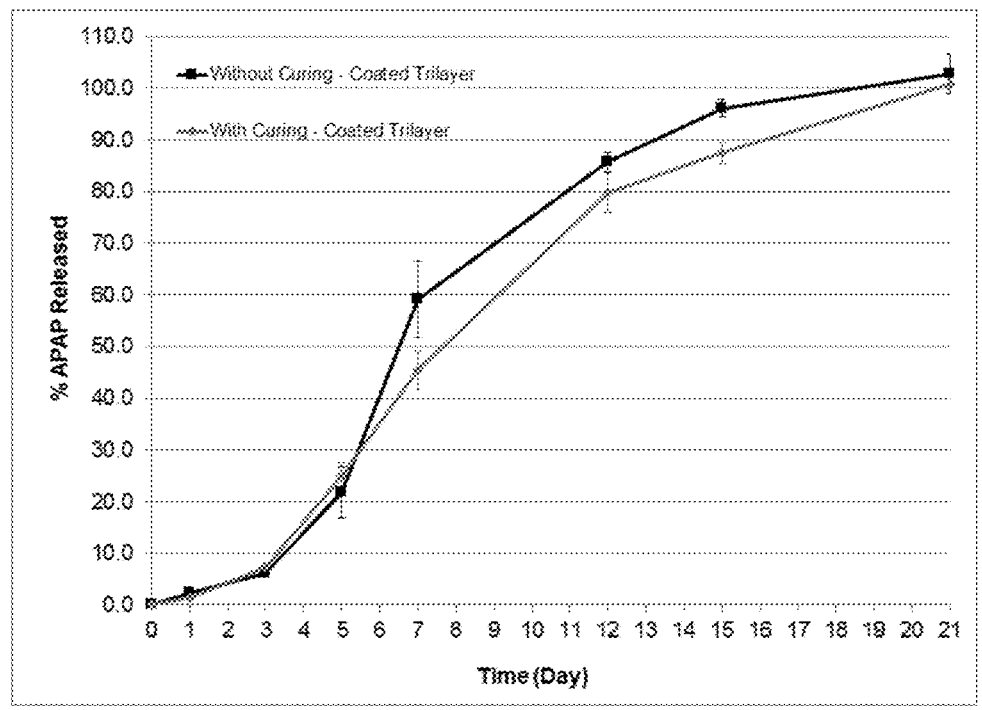
FIG. 5: Effect of curing at 73° C. for 10 minutes on the release of acetaminophen (APAP) from tri-layer (bio-adhesive layer, drug layer, hydrophobic layer and coating) wafer. The drug composition includes: (1) Drug layer composition: 5% APAP, 3% PEO 303, and 92% glycerol behenate, a total of 200 mg; (2) Hydrophobic layer composition: 100 mg glycerol behenate; and (3) Bio-adhesive layer composition: 50 mg PolyOx 303. The effects of curing on the APAP release showed that the curing and uncured samples had similar release profiles.

In some aspects, wafers or implants are provided that may be used to deliver a therapeutic agent to a resection cavity in the tissue of a subject, e.g., after surgical removal of tissue. For example, the wafer or implant may be used to deliver a chemotherapeutic agent to the brain of a subject after removal of a tumor from the brain of the subject. In some embodiments, the implant or wafer comprises multiple layers that may promote release of the therapeutic agent into the tissue, which may result in an improved therapeutic benefit.

In some aspects, a one or more anticancer compounds may be included in a wafer or implant of the present invention (e.g., for the treatment glioblastoma multiforme). In some embodiments, the anticancer compound included in the wafer or implant is a compound that does not cross the blood-brain barrier in sufficient amounts to exert a therapeutic response when delivered by oral or parenteral routes. Thus, in these embodiments, the wafer or implant can provide a particularly useful opportunity to deliver a therapeutic compound to or near to the site of surgery in the brain, where it would be otherwise difficult to deliver that compound due to the particular pharmacokinetics, etc. of the anti-cancer compound. Other adjunct non-therapeutic compounds may be included in the formulations, including absorption enhancing substances, antioxidants and other functional excipients. In some embodiments, little or no acidic byproducts are formed from the slow erosion of the solid dosage forms since the lipids and hydrophilic polymers can have an insignificant, minimal, or no effect on the pH of the surrounding biological fluid at the site of implantation. Thus, in accordance with one aspect, the present invention includes pharmaceutical implant compositions as anti-cancer drug delivery systems comprising as ingredients:

(a) anti-cancer compound(s);
(b) lipid compound(s);
(c) hydrophilic polymeric agent(s);
(d) optional pharmaceutical additives or excipients including enzymes or other active pharmaceutical ingredients;
(e) a hydrophobic top layer and/or coating; and
(f) an optional third layer comprising hydrophilic polymer(s).

The anti-cancer compounds in (a) (above) may include: cisplatin, topotecan, bevacizumab, doxorubicin, everolimus, paclitaxel, irinotecan, carboplatin, D-actinomycin, docetaxel, pitavastatin, methotrexate, temozolomide, epirubicin, cetuximab, copper chelating agents, carmustine, synthetic alkyl lysophospholipids, bioactive sulfated saponins, statins and the like. The nonionic lipid compounds in (b) (above) may include: glycerol behenate, fatty acid, cholesterol, glycerides, hydrogenated vegetable oils, tristearin, stearic acid, and the like. The water soluble hydrophilic polymeric pore forming agents included in the drug containing layer, (c), above) as well as polymers comprising the optional third layer in the implants, (f), above), include: polyethylene oxides, polysaccharides, proteins, oxidized cellulose polymers, polyanhydroglucuronic acid, poloxomers, chitosan, providone (PVP) and the like. Temozolomide is an alkalating agent that may be used, e.g., to treat malignant primary brain tumors. Temozolomide is generally 100% bioavailable in the systemic bloodstream of the patient when taken orally and is able to cross the blood-brain barrier, however the concentrations in the central nervous system have been reported to only be approximately 30% of plasma concentrations. Temozolomide has lipophilic properties and is a low molecular weight molecule. This compound typically must be present in the CNS in order for it to be converted to the active metabolite.

In some embodiments, a secondary therapeutic agent is included in the implant or wafer in addition to the anti-cancer agent. The implant wafer compositions may comprise an optional secondary therapeutic agents including, e.g., one or more antibiotics, statins, anti-fungals, anti-virals, pain medications, contraceptives, NSAIDS and steroids, to achieve simultaneous administration of the agents to a cancer patient. Such agents may be included with the anti-cancer compound in the wafer compositions of the present compositions or may be administered to the patient in a separate wafer.

The present invention also provides, in some aspects, methods of preparation of the wafers. For example, the pharmaceutical wafer compositions of the present invention may be processed by compression, hot-melt extrusion, injection molding, dry powder coating, hot-melt granulation, casting, evaporation technologies, dipping, spraying, or combinations of these methods. Elevated temperature curing is utilized to promote adhesion of the layers in the wafer.

In some aspects, implant wafers and methods provided herein may be used to maintain therapeutic concentrations of the drug at the site of implantation following surgical removal of the tumor, e.g., from about 1, 2, 3, 4, 5, 6, 7, 8, 9, 10 weeks, or 1, 2, 3, 4, 5, 6 months, or any range derivable therein. The particular rate of diffusion or release of the active agent, therapeutic agent, or anticancer agent may be varied or affected based the composition of the drug delivery system (e.g., particular polymers included in the implant or capsule, ratio of hydrophilic and hydrophobic polymers included, etc.) and the dose of the active moiety being delivered.

A. Hydrophilic Compound or Polymer

A variety of hydrophilic compounds or polymers may be included in an implant or wafer of the present invention. For example, in some embodiments, the hydrophilic compound is polyanhydroglucuronic acid. This material is currently used in surgery as a hemostatic agent to reduce blood clots and to promote wound healing. It is also an effective antibacterial agent. Polyanhydroglucuronic acid is an oxidized cellulose polymer with a basic unit of polyanhydroglucuronic acid. Related materials are described in U.S. Pat. No. 3,364,200. Polyanhydroglucuronic acid is the base material in the Surgicel® knitted fabric product that has has been used in surgery, including neurosurgery.

In some aspects of the present disclosure, the composition comprises a hydrophilic polymer. Hydrophilic polymers may contain polar or charged groups such that the polymer is soluble in water or aqueous mixtures. In particular, the hydrophilic polymers contain one or more groups, which can act as a hydrogen bond donor or acceptor or a charged group such as a carboxylic acid group or an amine group. Some non-limiting examples of hydrophilic polymers include: polyacrylamide, polyimines, polyacrylic acid, polyethylene oxide, polypropylene oxide, polyvinyl alcohol, polyvinylpyrrolidone, polyether, polymers of maleic anhydride, polyelectrolytes such as polystyrenesulfonates, or other water soluble groups such as cucurbit[n]uril.

In some embodiments, the hydrophilic polymer is a polyether. For examples, a polyether polymers that may be used in various embodiments include polyethylene oxide (also known as polyethylene glycol, PEG, or PEO) and polypropylene oxide (PPO). PEO is the polymeric form of ethylene glycol, while PPO is the polymeric form of propylene glycol. The formula of PEO and PPO, respectively, are shown below:

(I)

(II)

wherein the repeating unit, n, is an integer. In some aspects, the nomenclature used to describe PEO includes the average molecular weight of the polymer (e.g. PEO-400; PEO-500, PEO-600, etc.) In some embodiments, the molecular weight of PEO ranges from about 100,000 to about 7,000,000 daltons (e.g., PEO 303), more preferably from about 1,000,000 to about 7,000,000 daltons. In some embodiments, the molecular weight of the PEO is about 1e5, 2.5e5, 5e5, 1e6, 2e6, 3e6, 4e6, 5e6, 6e6, 7e6, 8e6 daltons, or any range derivable therein. As would be obvious to a person of skill in the art, the average molecular weight does not mean that any particular PEO or PPO molecule within the composition has the noted molecular weight but rather that the composition as a whole has the average molecular weight corresponding to that value. In some embodiments, the PEO or PPO molecule can have one or both of the terminal hydrogen atoms can be replaced with another group including but not limited to an alkyl group (e.g. a methyl group or an ethyl group).

In other embodiments, the composition comprises a hydrophilic polymer which is a natural biopolymer. The hydrophilic polymer may be a natural biopolymer such as, e.g., a polysaccharide. Polysaccharides are oligomers of sugars such as, e.g., glucose, fructose, galactose, xylose, and arabinose. Some non-limiting examples of polysaccharides which may be used include glycogen, amylose, amylopectin, arabinoxylan, cellulose, chitin or chitosan, or pectin. In some embodiments, the polysaccharide is chitin or chitosan.

In some embodiments, the wafer or implant may comprise one or more pharmaceutical additives or excipients that aid processing and can regulate the release of the active drug substance from the wafer. Such additives or excipients include, e.g., biocompatible surfactants, lipase, lecithin, polyols, proteins, enzymes, peptides and the like, and other suitable agents familiar to a person skilled in the art of preparing solid pharmaceutical dosage forms. The presence of lipase in the solid dosage form, may aid in the metabolism and elimination of fats and lipids at the implant site. The presence of absorption enhancing agents such as sodium lauryl sulfate and the polysorbates may also be included in the drug containing layer of the implant.

B. Hydrophobic Compounds or Agents

In some embodiments, the composition of one or more of the layers contains a hydrophobic compound or hydrophobic agent. These hydrophobic compounds may include steroids, fatty acids, and/or glycerides. When a lipid is used in the wafer or capsule, it is anticipated that the lipid may be used in conjunction with or substituted for one or more the hydrophobic compounds described herein (e.g. a fatty acid or glyceride may be included instead of the lipid).

Steroids are compounds which contain a four ring fused structure as shown below:

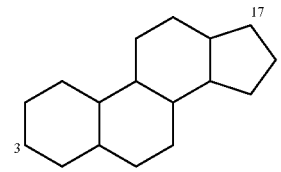

also known as hexadecahydro-1H-cyclopenta[a]phenanthrene. The steroids described herein may have a hydroxy or oxo substituted on carbon atom 3 and are commonly substituted with an alkyl group at one or more of carbon atoms 10, 13 and 17. In some embodiments, the hydroxy substitution at position 3 of the steroid is in the β orientation. In some embodiments, the alkyl groups are at carbon atom 17. Without wishing to be bound by any theory, it is believed that steroids with any substituents on the ring, other orientations, salt forms and other known variations of the basic ring may be used in the compositions described herein. Some non-limiting examples of steroids include cholesterol, androstenolone, androsterone, brassicasterol, calciferol, campesterol, cholestanol, cholestenone, coprostene, cortisone, demosterol, diosgenin, dihydrocalciferol, ergosterol, epicholestanol, estrone, estradiol, fucosterol, hecogenin, hexahydrolumi sterol, lanosterol, lumisterol, pregnenolone, progesterone, oestrone, sarsasapogenin, sitosterol, smilagenin, spinastenol, stigmasterol, stigmastanol, testosterone, tigogenin and tomatidine. In some embodiments, the steroids used herein is cholesterol.

In other embodiments, the compositions of the present disclosure may include fatty acids and/or glycerides. Fatty acids are long chain alkyl groups with a carboxylic acid at one end. In some embodiments, alkyl group of the fatty acid has from 6 to 24 carbon atoms. These fatty acids which do not contain any double bonds are saturated fatty acids. Fatty acids may also contain one or more double bonds in the alkyl group. Fatty acids containing one or more double bonds are unsaturated fatty acids. If double bonds are present in the fatty acid, these double bonds may be in the cis orientation. The alkyl group may comprise 1, 2, or 3 double bonds. Some non-limiting examples of fatty acids include: butyric acid, caproic acid, caprylic acid, capric acid, lauric acid, myristic acid, palmitic acid, margaric acid, stearic acid, arachidic acid, behenic acid, lignoceric acid, palmitoleic acid, oleic acid, elaidic acid, vaccenic acid, gondoic acid, erucic acid, mead acid, linoleic acid, α-linoleic acid, stearidonic acid, γ-linoleic acid, arachidonic acid, eicosapentaenoic acid, docosahexaenoic acid, or nervonic acid.

In other embodiments, the compositions of the present disclosure may include glycerides. Glycerides comprise esters of the glycerol and one, two, or three fatty acids of the described herein. As would be understood by a person of skill in the art, a monoglyceride is a glycerol esterified to one fatty acid, a diglyceride is a glycerol esterified to two fatty acids, and a triglyceride is a glyceride esterified to three fatty acids. It is also contemplated that the glycerides may be substituted with one or more other groups such as an amino acid, choline, a phosphate group, an alkylamino, or any combination of theses groups.

The term "unit dose" or "dosage" refers to physically discrete units suitable for use in a subject, each unit containing a predetermined quantity of the therapeutic composition calculated to produce the desired responses discussed above in association with its administration, i.e., the appropriate route and treatment regimen. The quantity to be administered, both according to number of treatments and unit dose, depends on the effect desired. The actual dosage amount of a composition of the present embodiments administered to a patient or subject can be determined by physical and physiological factors, such as body weight, the age, health, and sex of the subject, the type of disease being treated, the extent of disease penetration, previous or concurrent therapeutic interventions, idiopathy of the patient, the route of administration, and the potency, stability, and toxicity of the particular therapeutic substance. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 milligram/kg/body weight or more per administration, and any range derivable therein. In non-limiting examples of a derivable range from the numbers listed herein, a range of about 5 milligram/kg/body weight to about 100 milligram/kg/body weight, about 5 microgram/kg/body weight to about 500 milligram/kg/body weight, etc., can be administered, based on the numbers described above. The practitioner responsible for administration will, in any event, determine the concentration of active ingredient(s) in a composition and appropriate dose(s) for the individual subject. In certain embodiments, the compositions and methods of the present embodiments involve administration of an implant in a resection cavity as described herein in combination with a second or additional therapy. Such therapy can be applied in the treatment of any disease that is responsive to CDC. For example, the disease may be cancer.

C. Implant Characteristics and Production

In some embodiments, the multilayered wafer implants of the present invention may weigh between about 50 mg and 800 mg, more preferably about 100-400 mg. The diameter of the wafer may vary from about 0.25-3 centimeters, with one to two centimeters being more preferred. The thickness of these wafers may vary from about 0.5-5.0 mm, with 0.75 mm to 2.0 mm being more preferred. The drug content may depend upon the processing and physical and chemical properties of the drug, polymers and lipids as well as the compressibility and thermal stability. The potency of the wafers may vary from about 0.1% to 60%, with about 5-30% being more preferred. The shape of the wafer implants can be prepared in a variety of configurations such as, e.g., circular, square, rectangular or oblong, and the implants can be cut or split in half or into smaller particles as desired by the neurosurgeon at the time of implantation. In addition, the wafers may have surfaces that are concave or convex. The wafers can be sterilized, e.g., by the use of gamma radiation, ethylene oxide, or electron beam radiation. Bilayered and trilayered wafers can be prepared by compression on a tablet press or a Carver press. A melt granulated powder blend of the lipid and drug components are physically blended with hydrophilic polymer for the drug containing layer and may be first added to the die, followed by the wax or lipid used as the top layer in the implant. The compressed wafer may then be heated at elevated temperatures of about 65° C. for 2-4 hours or 73° C. for 10 minutes or a temperature between the two. The curing temperature should be a few degrees below the melting point of the hydrophobic retardant, to adhere the hydrophobic layer to the drug containing layer.

Alternately, in some embodiments, for the three layered wafer, the first component that is present in the die is the hydrophilic polymer followed by the powder blend containing the chemotherapeutic agent containing layer and finally the hydrophobic powder is added. The compressed wafer may then be heat treated as described above.

Additionally, a hydrophobic coating may be applied through a dipping, spraying, or similar technique to further promote unidirectionality and slow drug release. In some embodiments, the coating covers the wafers on all or substantially all sides where drug release is non-desirable. In some embodiments, the bioadhesive layer is left mostly or completely uncoated, and the backing and sides are covered with the hydrophobic coating.

In some embodiments, the hydrophilic polymeric layer be prepared by hot melt extrusion. A molten dispersion comprising the lipid, hydrophilic polymer, chemotherapeutic agent and other optional ingredients may then applied to the film and allowed to cool. The final layer of molten lipid or wax may then be applied. The resulting film may then be cut into wafers of desired dimensions. The resulting wafers may then be cured at elevated temperature for up to about 4 hours. For example, the resulting wafer is cured for a time period from about 5 minutes to about 4 hours, or from about 2 hours to about 4 hours.

D. Indications

In some preferred embodiments, an implant is applied to a resection cavity (e.g., in the brain) after surgical removal of a cancerous tissue. In other embodiments, the implant may be applied to a resection cavity (e.g., in the brain or other portion of the body) after removal of a non-cancerous tissue.

A variety of cancers may be treated using an implant of the present invention. A tumor that is removed from the brain of a subject (e.g., a human patient) may be cancerous, precancerous, or benign. In some embodiments, the tumor is cancerous. The tumor in the brain may have originated in the brain of the subject (e.g., a brain cancer) or the tumor may have originated in a different part of the body (e.g., a metastatic cancer that has originated in some other part of the body but has travelled to the brain). Tumors for which the present treatment methods are useful include any malignant cell type, such as those found in a solid tumor or a hematological tumor. Exemplary solid tumors can include, but are not limited to, a tumor of an organ selected from the group consisting of pancreas, colon, cecum, stomach, brain, head, neck, ovary, kidney, larynx, sarcoma, lung, bladder, melanoma, prostate, and breast. Exemplary hematological tumors include tumors of the bone marrow, T or B cell malignancies, leukemias, lymphomas, blastomas, myelomas, and the like. Further examples of cancers that may be treated using the methods provided herein include, but are not limited to, carcinoma, lymphoma, blastoma, sarcoma, leukemia, squamous cell cancer, lung cancer (including small-cell lung cancer, non-small cell lung cancer, adenocarcinoma of the lung, and squamous carcinoma of the lung), cancer of the peritoneum, hepatocellular cancer, gastric or stomach cancer (including gastrointestinal cancer and gastrointestinal stromal cancer), pancreatic cancer, glioblastoma, cervical cancer, ovarian cancer, liver cancer, bladder cancer, breast cancer, colon cancer, colorectal cancer, endometrial or uterine carcinoma, salivary gland carcinoma, kidney or renal cancer, prostate cancer, vulval cancer, thyroid cancer, various types of head and neck cancer, melanoma, superficial spreading melanoma, lentigo malignant melanoma, acral lentiginous melanomas, nodular melanomas, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's macroglobulinemia), chronic lymphocytic leukemia (CLL), acute lymphoblastic leukemia (ALL), Hairy cell leukemia, multiple myeloma, acute myeloid leukemia (AML) and chronic myeloblastic leukemia.

The cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; hodgkin's disease; hodgkin's; paragranuloma; malignant lymphoma, small lymphocytic; malignant lymphoma, large cell, diffuse; malignant lymphoma, follicular; mycosis fungoides; other specified non-hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

The methods and compositions, including combination therapies, may enhance the therapeutic or protective effect, and/or increase the therapeutic effect of another anti-cancer or anti-hyperproliferative therapy. Therapeutic and prophylactic methods and compositions can be provided in a combined amount effective to achieve the desired effect, such as the killing of a cancer cell and/or the inhibition of cellular hyper proliferation. This process may involve administering a polypeptide or antibody and a second therapy. The second therapy may or may not have a direct cytotoxic effect. For example, the second therapy may be an agent that upregulates the immune system without having a direct cytotoxic effect. A tissue, tumor, or cell can be exposed to one or more compositions or pharmacological formulation(s) comprising one or more of the agents (e.g., a polypeptide or an anti-cancer agent), or by exposing the tissue, tumor, and/or cell with two or more distinct compositions or formulations, wherein one composition provides 1) a polypeptide or antibody, 2) an anti-cancer agent, or 3) both a polypeptide or antibody and an anti-cancer agent.

Also, it is contemplated that such a combination therapy can be used in conjunction with chemotherapy, radiotherapy, surgical therapy, or immunotherapy.

The terms "contacted" and "exposed," when applied to a cell, are used herein to describe the process by which a therapeutic polypeptide or antibody and a chemotherapeutic or radio therapeutic agent are delivered to a target cell or are placed in direct juxtaposition with the target cell. To achieve cell killing, for example, both agents are delivered to a cell in a combined amount effective to kill the cell or prevent it from dividing.

E. Combination Therapies

An implant in a resection cavity as described herein may be administered before, during, after, or in various combinations relative to an anti-cancer treatment. The administrations may be in intervals ranging from concurrently to minutes to days to weeks. In embodiments where an implant in a resection cavity as described herein is provided to a patient separately from an anti-cancer agent, one would generally ensure that a significant period of time did not expire between the time of each delivery, such that the two compounds would still be able to exert an advantageously combined effect on the patient. In such instances, it is contemplated that one may provide a patient with the polypeptide and the anti-cancer therapy within about 12 to 24 or 72 h of each other and, more particularly, within about 6-12 h of each other. In some situations it may be desirable to extend the time period for treatment significantly where several days (2, 3, 4, 5, 6, or 7) to several weeks (1, 2, 3, 4, 5, 6, 7, or 8) lapse between respective administrations.

In certain embodiments, a course of treatment will last 1-90 days or more (this range includes intervening days). It is contemplated that one agent may be given on any day of day 1 to day 90 (this range includes intervening days) or any combination thereof, and another agent is given on any day of day 1 to day 90 (this range includes intervening days) or any combination thereof. Within a single day (24-hour period), the patient may be given one or multiple administrations of the agent(s). Moreover, after a course of treatment, it is contemplated that there is a period of time at which no anti-cancer treatment is administered. This time period may last 1-7 days, and/or 1-5 weeks, and/or 1-12 months or more (this such range includes intervening days), depending on the condition of the patient, such as their prognosis, strength, health, etc. It is expected that the treatment cycles would be repeated as necessary.

Various combinations may be employed. For the example below a polypeptide or antibody is "A" and an anti-cancer therapy is "B":

A/B/AB/A/BB/B/AA/A/BA/B/BB/A/AA/B/B/BB/A/B/B

B/B/B/A B/B/A/B A/A/B/B A/B/B/A/BA/B/B/AB/B/A/A

B/A/B/A B/A/A/B A/A/A/BB/A/A/AA/B/A/AA/A/B/A

Administration of any implant in a resection cavity as described herein or therapy of the present embodiments to a patient will follow general protocols for the administration of such compounds, taking into account the toxicity, if any, of the agents. Therefore, in some embodiments there is a step of monitoring toxicity that is attributable to combination therapy.

A. Chemotherapy

A wide variety of chemotherapeutic agents may be used in accordance with the present embodiments. For example, a chemotherapeutic may be comprised in an implant (e.g., a drug wafer implant comprising a lipid and a hydrophobic polymer). The drug may be a chemotherapeutic. It is envisioned that virtually any chemotherapy or chemotherapeutic agent known may be included in an implant (e.g., a drug wafer implant) or used in various embodiments of the present invention. In some embodiments, the chemotherapeutic agent may be included in a drug wafer implant to achieve a local concentration in the brain (e.g., near the injection site) that is significantly higher than the systemic concentration that one would typically be able to achieve by systemic administration of the chemotherapeutic agent. Alternately, an implant in a resection cavity as described herein may be used in combination with administration or a chemotherapy agent or other therapy as described herein.

The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis.

Examples of chemotherapeutic agents include alkylating agents, such as thiotepa and cyclosphosphamide; alkyl sulfonates, such as busulfan, improsulfan, and piposulfan; aziridines, such as benzodopa, carboquone, meturedopa, and uredopa; ethylenimines and methylamelamines, including altretamine, triethylenemelamine, trietylenephosphoramide, triethiylenethiophosphoramide, and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards, such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, and uracil mustard; nitrosureas, such as carmustine, chlorozotocin, fotemustine, lomustine, nimustine, and ranimnustine; antibiotics, such as the enediyne antibiotics (e.g., calicheamicin, especially calicheamicin gammaI1 and calicheamicin omegaI1); dynemicin, including dynemicin A; bisphosphonates, such as clodronate; an esperamicin; as well as neocarzinostatin chromophore and related chromoprotein enediyne antiobiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, and zorubicin; anti-metabolites, such as methotrexate and 5-fluorouracil (5-FU); folic acid analogues, such as denopterin, pteropterin, and trimetrexate; purine analogs, such as fludarabine, 6-mercaptopurine, thiamiprine, and thioguanine; pyrimidine analogs, such as ancitabine, azacitidine, 6-azauridine, carmofur, cytarabine, dideoxyuridine, doxifluridine, enocitabine, and floxuridine;

androgens, such as calusterone, dromostanolone propionate, epitiostanol, mepitiostane, and testolactone; anti-adrenals, such as mitotane and trilostane; folic acid replenisher, such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids, such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSKpolysaccharide complex; razoxane; rhizoxin; sizofiran; spirogermanium; tenuazonic acid; triaziquone; 2,2',2''-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; taxoids, e.g., paclitaxel and docetaxel gemcitabine; 6-thioguanine; mercaptopurine; platinum coordination complexes, such as cisplatin, oxaliplatin, and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DMFO); retinoids, such as retinoic acid; capecitabine; carboplatin, procarbazine, plicomycin, gemcitabien, navelbine, farnesyl-protein transferase inhibitors, transplatinum, and pharmaceutically acceptable salts, acids, or derivatives of any of the above.

B. Radiotherapy

Other factors that cause DNA damage and have been used extensively include what are commonly known as γ-rays, X-rays, and/or the directed delivery of radioisotopes to tumor cells. Other forms of DNA damaging factors are also contemplated, such as microwaves, proton beam irradiation (U.S. Pat. Nos. 5,760,395 and 4,870,287), and UV-irradiation. It is most likely that all of these factors affect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

C. Immunotherapy

The skilled artisan will understand that immunotherapies may be used in combination or in conjunction with methods of the embodiments. In the context of cancer treatment, immunotherapeutics, generally, rely on the use of immune effector cells and molecules to target and suppress immune cells. Blinatumomab (Blincyto®) is such an example. Checkpoint inhibitors, such as, for example, ipilumimab, are another such example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

In one aspect of immunotherapy, the tumor cell must bear some marker that is amenable to targeting, i.e., is not present on the majority of other cells. Many tumor markers exist and any of these may be suitable for targeting in the context of the present embodiments. Common tumor markers include CD20, carcinoembryonic antigen, tyrosinase (p97), gp68, TAG-72, HMFG, Sialyl Lewis Antigen, MucA, MucB, PLAP, laminin receptor, erb B, and p155. An alternative aspect of immunotherapy is to combine anticancer effects with immune stimulatory effects. Immune stimulating molecules also exist including: cytokines, such as IL-2, IL-4, IL-12, GM-CSF, gamma-IFN, chemokines, such as MIP-1, MCP-1, IL-8, and growth factors, such as FLT3 ligand.

Examples of immunotherapies currently under investigation or in use are immune adjuvants, e.g., *Mycobacterium bovis, Plasmodium falciparum*, dinitrochlorobenzene, and aromatic compounds (U.S. Pat. Nos. 5,801,005 and 5,739,169; Hui and Hashimoto, 1998; Christodoulides et al., 1998); cytokine therapy, e.g., interferons α, β, and γ, IL-1, GM-CSF, and TNF (Bukowski et al., 1998; Davidson et al., 1998; Hellstrand et al., 1998); gene therapy, e.g., TNF, IL-1, IL-2, and p53 (Qin et al., 1998; Austin-Ward and Villaseca, 1998; U.S. Pat. Nos. 5,830,880 and 5,846,945); and monoclonal antibodies, e.g., anti-CD20, anti-ganglioside GM2, and anti-p185 (Hollander, 2012; Hanibuchi et al., 1998; U.S. Pat. No. 5,824,311). It is contemplated that one or more anti-cancer therapies may be employed with the antibody therapies described herein.

D. Surgery

Approximately 60% of persons with cancer will undergo surgery of some type, which includes preventative, diagnostic or staging, curative, and palliative surgery. Curative surgery includes resection in which all or part of cancerous tissue is physically removed, excised, and/or destroyed and may be used in conjunction with other therapies, such as the treatment of the present embodiments, chemotherapy, radiotherapy, hormonal therapy, gene therapy, immunotherapy, and/or alternative therapies. Tumor resection refers to physical removal of at least part of a tumor. In addition to tumor resection, treatment by surgery includes laser surgery, cryosurgery, electrosurgery, and microscopically-controlled surgery (Mohs' surgery).

Upon excision of part or all of cancerous cells, tissue, or tumor, a cavity may be formed in the body. Treatment may be accomplished by perfusion, direct injection, or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

E. Other Agents

It is contemplated that other agents may be included in a drug wafer implant or used in combination with certain aspects of the present embodiments to improve the therapeutic efficacy of treatment. These additional agents include agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Increases in intercellular signaling by elevating the number of GAP junctions may increase the anti-hyperproliferative effects on the neighboring hyperproliferative cell population. In other embodiments, cytostatic or differentiation agents can be used in combination with certain aspects of the present embodiments to improve the anti-hyperproliferative efficacy of the treatments. Inhibitors of cell adhesion are contemplated to improve the efficacy of the present embodiments. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with certain aspects of the present embodiments to improve the treatment efficacy.

II. Kits

Certain aspects of the present invention may provide kits, such as therapeutic kits. For example, a kit may comprise one or more pharmaceutical composition as described herein and optionally instructions for their use. Kits may also comprise one or more devices for accomplishing administration of such compositions. For example, a subject kit may comprise a pharmaceutical composition and wafer or implant for accomplishing administration of a therapeutic agent into a tissue in a subject, e.g., a brain tissue in a resection cavity in subject.

Kits may comprise a container with a label. Suitable containers include, for example, bottles, vials, and test tubes. The containers may be formed from a variety of materials, such as glass or plastic. The container may hold a composition that includes a polypeptide that is effective for therapeutic or non-therapeutic applications, such as described above. The label on the container may indicate that the composition is used for a specific therapy or non-therapeutic application, and may also indicate directions for either in vivo or in vitro use, such as those described above. The kit of the invention will typically comprise the container described above and one or more other containers comprising materials desirable from a commercial and user standpoint, including buffers, diluents, filters, needles, syringes, and package inserts with instructions for use.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Multi-Layered Implants

In the following examples, Layer 1 is always the side positioned proximal, or directly against the brain tissue in the resection cavity.

An embodiment of the present invention provides a wafer or composition comprising:

| Layer 1 | Polyethylene oxide 4M | 10% |
|---|---|---|
| Layer 2 | | 80% |
| | paxlitaxel | 12% |
| | glyceryl behenate | 60% |
| | stearic acid | 6% |
| | polyethylene oxide 0.9M | 22% |
| Layer 3 | | 10% |
| | Stearic acid | 5% |
| | Glyceryl behenate | 5% |

The components for Layer 2 are first passed through a 60 mesh screen to remove lumps and then blended in a twin shell blender for 5 minutes. The three layered wafer is compressed and used a described previously. These technologies and methods are familiar to a person of ordinary skill in the art.

A further embodiment of the present invention provides a bilayered wafer implant composition comprises the following ingredients:

| Layer 1. | | 85% |
|---|---|---|
| | carboplatin | 7.5% |
| | docetaxel | 12.5% |
| | glycerol behenate | 43% |
| | polyethylene oxide 1M | 37% |
| Layer 2. | Stearic Acid | 15% |

The components of Layer 1 are added first to the die in the tablet press, followed by the stearic acid. These wafers were compressed and then heated at 68° C. for 3 hours.

A further embodiment of the present invention for the manufacture of wafers or tablets, comprises the following composition:

| a. | temozolomide | 75 mg |
|---|---|---|
| b. | stearic acid | 25 mg |
| c. | lipase | 3 mg |
| d. | cholesterol | 12 mg |
| e. | glycerol behenate | 70 mg |
| f. | poloxamer F-68 | 15 mg |
| g. | polyanhydroglucuronic acid | 50 mg |

The wafer compositions of this example can be processed according to methods known to a person who is already skilled in the art as exemplified in Method 1. Using the tablet compression method, the powders are first passed through a 100 mesh screen and then dry blended for 5 minutes prior to compression. Using a Carver press or tablet press, the components for the drug containing layer are first added to the tablet die followed by the hydrophobic powder as described in Method 1. The resulting compositions were then cured at 65° C. for 3 hours. Implant compositions were prepared according to the Methods as described below.

The components of the drug containing layers in the compositions of Methods 2 and 3 can also be processed by injection molding and then milled into finer particles prior to compression into wafers that are 1.5 cm in diameter and 3 mm thick. The implants are then cured for 2 hours at 65° C.

A trilayered implant composition according to the present invention is composed of:

| Layer 1 | polyethylene oxide 1M | 40 mg |
|---|---|---|
| Layer 2 | cetuximab | 35 mg |
| | everolimus | 40 mg |
| | chitosan | 10 mg |
| | polyoxyethylene oxide 0.9M | 65 mg |
| | glycerol behenate | 100 mg |
| Layer 3. | Glycerol behenate | 20 mg |
| | Cholesterol | 8 mg |

The compressed wafers were cured at 60° C. for 8 hours.

Another preferred embodiment of the present invention has a composition of:

| Layer 1 | Chitosan | 8% |
|---|---|---|
| | Polyethylene oxide 4M | 6% |

-continued

| Layer 2 | | 70% |
| --- | --- | --- |
| | cisplatin | 20% |
| | glyceryl behenate | 40% |
| | stearic acid | 10% |
| | polyethylene oxide 0.5M | 20% |
| | polyanhydroglucuronic acid | 10% |
| Layer 3 | Glycerol behenate | 14% |

The polyanhydroglucuronic acid (Surgicel®) was cryogenically processed and then ground into fine powder. The composition is wet granulated with purified water, dried, passed through a 20 mesh screen and then processed into 500 mg wafers according to the processing methods outlined in Method 1. Circular wafers were then cured at 65° C. for 2 hours.

Bevacizumab (20% Layer 2) and Methotraxate (20% Layer 2) implants were prepared according to Method 6 and heat cured at 70° C. for 2 hours.

A further embodiment of the present invention for the manufacture of a trilayered film composition comprising the following ingredients:

| Layer 1 | Polyethylene oxide 4M | 20% |
| --- | --- | --- |
| Layer 2 | | 70% |
| | Irinotecan | 8% |
| | Lipase | 0.5% |
| | Stearic acid | 14% |
| | Glyceryl behenate | 49% |
| | Pitavastatin | 3.5% |
| | Poloxamer F68 | 10% |
| | Polyethylene oxide 0.9M | 15% |
| Layer 3 | Glyceryl behenate | 10% |

A film of polyethylene oxide is prepared by hot melt extrusion at process temperatures in the extruder ranging from 75° C. to 95° C. To this film, a molten composition is evenly spread and then cooled to room temperature. The glyceryl behenate in Layer 3 is melted and added onto the drug containing layer. The film is cooled and then cut into suitable sized wafers that are then heat cured at 68° C. for 4 hours.

Method 1. An embodiment of the present invention provides a trilayer wafer or composition comprising:

| Layer 1 | Polyethylene oxide 7M | 50 mg |
| --- | --- | --- |
| Layer 2 | | 200 mg |
| | paclitaxel | 8 mg |
| | glyceryl behenate | 185 mg |
| | polyethylene oxide 7M | 7 mg |
| Layer 3 | glyceryl behenate | 100 mg |

All inert components were passed through a 70 mesh screen. A trilayered wafer was prepared by first adding the polyethylene oxide 7M (Layer 1) to the tablet die, followed by the powder blend containing paclitaxel, glyceryl behenate and the polyethylene oxide (Layer 2). The glyceryl behenate (Layer 3) was first melted at 120° C., cooled and passed through a 60 mesh screen and then added to the die prior to compression into a trilayered wafer. The sides of the circular trilayered wafer and the top lipophilic wax layer (Layer 3) were then coated with molten glyceryl behenate at 98° C., leaving the bioadhesive layer (Layer 1) uncoated and was then cured at approximately 72° C. for ten minutes.

Method 2. A composition of Method 1 was prepared where the three powders of the drug containing layer (Layer 2) were blended together and then melt granulated by heating the powder blend to approximately 120° C. for five minutes. The resulting mass was then cooled, milled and passed through a 60 mesh screen, before incorporation into the three layer wafer using the method described in Method 1.

Method 3. A further embodiment of the present invention involves the composition of Method 1, when the glyceryl behenate and paclitaxel in Layer 2 are first blended together and then melt granulated by heating the powder to 120° C. for five minutes. When this mass was cooled and passed through a 60 mesh screen, the polyethylene oxide component of Layer 2 was then added to form the final powder blend for Layer 2, which was then incorporated into the trilayered wafer formulation and then processed according to the method described in Method 1.

Method 4. A further embodiment of the present invention provides a trilayered wafer implant composition of Method 3 where the sides and top lipophilic layer of the wafer were coated, in lieu of glyceryl behenate, with an organic solution of a Resomer® RG 756 S biodegradable polymer (5% W/W in acetone), (Resomer® RG 756S) leaving the bioadhesive layer (Layer 1), uncoated, and cured at 72° C. for 10 minutes.

Method 5. A further embodiment of the present invention provided a coated three layered wafer composition to contain carboplatin 3 mg, and docetaxel 5 mg, as the active ingredients in a 350 mg trilayered wafer, prepared by the method outlined in Method 3.

Method 6. A further embodiment of the present invention provides for the manufacture of trilayered wafers each comprising the following composition:

| Layer 1 | polyethylene oxide 7M | 15 mg |
| --- | --- | --- |
| Layer 2 | dexamethasone sodium phosphate | 8 mg |
| | paclitaxel | 20 mg |
| | glyceryl behenate | 162 mg |
| | stearic acid | 7 mg |
| | polyethylene oxide 7M | 8 mg |
| Layer 3 | glyceryl behenate | 100 mg |

All inert components were passed through a 70 mesh screen. The trilayered wafer was prepared by first adding the polyethylene oxide 7M (Layer 1) to a tablet die, followed by the powder blend containing the two active ingredients, along with the glyceryl behenate and the stearic acid in the Layer 2 composition that had previously been melt granulated by heating the powders of Layer 2 to 120° C. for five minutes. When this mass was cooled and passed through a 60 mesh screen, the polyethylene oxide component of Layer 2 was then added to form the final powder blend for Layer 2, which was then incorporated into the trilayered wafer formulation. The melt granulated glyceryl behenate (Layer 3) was then added to the die, prior to compression into a trilayered wafer. The sides of the circular trilayered wafer and the top lipophilic wax layer (Layer 3) were then coated with molten glyceryl behenate leaving the bioadhesive layer (Layer 1) uncoated.

Method 7. A further embodiment of the present invention of composition in Example 6 provides a trilayered wafer that was cured at approximately 72° C. for ten minutes.

Method 8. A further embodiment of the present invention provides for the manufacture of trilayered wafers or tablets each comprising the following composition:

| Layer 1. | polyethylene oxide 7M | 50 mg |
| --- | --- | --- |
| Layer 2. | temozolomide | 25 mg |

|        |                          |        |
|--------|--------------------------|--------|
|        | stearic acid             | 25 mg  |
|        | lipase                   | 2 mg   |
|        | cholesterol              | 10 mg  |
|        | glyceryl behenate        | 105 mg |
|        | poloxamer F-68           | 8 mg   |
|        | polyanhydroglucuronic acid | 25 mg |
| Layer 3 | stearic acid            | 40 mg  |
|        | glyceryl behenate        | 60 mg  |

All inert components were passed through a 70 mesh screen, except for the polyanhydroglucuronic acid which was passed through a 40 mesh screen. A trilayered wafer was prepared by first adding the polyethylene oxide 7M (Layer 1) to the tablet die, followed by the powders of the drug containing layer (Layer 2), which had been previously blended together and wet granulated with water and then melt granulated by heating the powder blend to approximately 120° C. for five minutes. The resulting mass was then cooled and milled before passing through a 40 mesh screen. The powder blend of stearic acid and glyceryl behenate (Layer 3) was melt granulated and cooled before passing through a 60 mesh screen and then added to the die prior to compression into a trilayered wafer. The sides and the top lipophilic wax layer (Layer 3) of the circular trilayered wafer were then coated with molten glyceryl behenate, leaving the bioadhesive layer (Layer 1) uncoated. The coated wafer was then cured at approximately 74° C. for 8 minutes.

Method 9. A further embodiment of the present invention provides for the uncoated trilayered wafer of Method 6, to contain irinotecan 12 mg in place of the temozolomide. The sides and the top lipophilic wax layer (Layer 3) of the trilayered wafer were then coated with a 5% w/w acetone solution of PLGA (Resomer® RG 756S), and cured at 60° C. for eight minutes.

Method 10. A further embodiment of the present invention provides for the manufacture of trilayered wafers, each comprising the following composition as described below.

|        |                          |         |
|--------|--------------------------|---------|
| Layer 1 | chitosan                | 30 mg   |
|        | polyethylene glycol 100,000 | 5 mg |
|        | polyethylene oxide 1M    | 15 mg   |
| Layer 2 | carboplatin              | 3 mg    |
|        | atorvastin               | 1.5 mg  |
|        | cisplatin                | 4 mg    |
|        | stearic acid             | 212 mg  |
|        | lipase                   | 1.5 mg  |
|        | glyceryl tristearate     | 20 mg   |
|        | polyethylene oxide 0.9M  | 8 mg    |
| Layer 3 | stearic acid             | 20 mg   |
|        | glyceryl behenate        | 80 mg   |

All inert components were prescreened to remove lumps and aggregates. A trilayered wafer was prepared by first blending the components of Layer 1, including chitosan, polyethylene glycol, and polyethylene oxide, into a uniform composition. This material was then added to the tablet die.

The three active ingredients in Layer 2, were blended together and then incorporated with the remaining powders in Layer 2 and melt granulated by heating the powder blend to approximately 120° C. for ten minutes.

The resulting mass was cooled and milled by passing through a 60 mesh screen. The granulation from Layer 2 was then added to the tablet die, followed by the stearic acid and glyceryl behenate melt granulated powder blend that formed Layer 3, prior to compression.

The sides of the circular trilayered wafer and the top lipophilic wax layer (Layer 3) were then coated with molten glyceryl behenate, leaving the bioadhesive layer (Layer 1) uncoated. The coated wafers were then heat treated at 60° C. for 5 minutes.

Method 11. A further embodiment of the present invention provides a bilayered wafer implant composition comprised of the following ingredients:

|        |                          |         |
|--------|--------------------------|---------|
| Layer 1 | carboplatin             | 7 mg    |
|        | docetaxel                | 4 mg    |
|        | glyceryl behenate        | 214 mg  |
|        | polyethylene oxide 7M    | 13 mg   |
|        | lipase                   | 2 mg    |
| Layer 2 | palmitic acid           | 48 mg   |
|        | glyceryl behenate        | 112 mg  |

The inert components of Layer 1 were dry blended and then passed through an 70 mesh screen. Using water as the granulating agent, the powder blend was then wet granulated. The granules were dried for four hours at 60° C., were passed through a 60 mesh screen and then melt granulated by heating the power blend at 110° C. for four minutes. The resulting mass was cooled and then passed through a 30 mesh screen. The bilayered wafers were prepared by adding the components from Layer 1 to the tablet die, followed by the powder from Layer 2 to the tablet die, in compositions as described above. The bilayered wafers were then compressed and cured at 62° C. for eight minutes.

Method 12. A further example of the present invention provides for the uncoated bilayered wafers of Method 11 to have the sides and the top lipophilic wax layer (Layer 2) of the bilayered wafer coated with molten glyceryl behenated, leaving the bioadhesive layer (Layer 1) uncoated. The coated wafers were then heat treated at 70° C. for 5 minutes.

Method 13. A further embodiment of the present invention provides a bilayered wafer implant composition comprised of the following ingredients:

|        |                          |         |
|--------|--------------------------|---------|
| Layer 1 | paclitaxel              | 11 mg   |
|        | dexamethasone sodium phosphate | 7 mg |
|        | glyceryl behenate        | 207 mg  |
|        | polyethylene oxide 7M    | 13 mg   |
|        | lipase                   | 2 mg    |
| Layer 2 | palmitic acid           | 48 mg   |
|        | glyceryl behenate        | 112 mg  |

The inert components of Layer 1 were dry blended and then passed through an 70 mesh screen. Using water as the granulating agent, the powder blend was then wet granulated. The dried granules were passed through a 60 mesh screen and then melt granulated by heating the power blender 110° C. for four minutes. The resulting mass was cooled and then passed through a 30 mesh screen. The bilayered wafers were prepared by adding the components from Layer 1 to the tablet die, followed by the melt granulated powder from Layer 2 to the tablet die, in compositions as described above. The bilayered wafers were then compressed and heated at 70° C. for eight minutes.

Method 14. A further example of the present invention provides for the uncoated trilayered wafers of Method 9 to have the sides and the top lipophilic wax layer (Layer 2) of the bilayered wafer coated with molten glyceryl behenated, leaving the bioadhesive layer (Layer 1) uncoated. The coated wafers were then heat treated at 70° C. for 5 minutes.

Method 15. A further embodiment of the present invention provides a trilayered implant composition comprising the following ingredients:

| Layer 1 | polyethylene oxide 1M | 15 mg |
|---|---|---|
| | Polyethylene oxide 7M | 35 mg |
| Layer 2 | bevacizumab | 2 mg |
| | cetuximab | 1.5 mg |
| | everolimus | 4.5 mg |
| | glyceryl behenate | 185 mg |
| | polyethylene oxide (100,000 MW) | 7 mg |
| Layer 3 | glyceryl behenate | 85 mg |
| | stearic acid | 10 mg |
| | Cholesterol | 5 mg |

All inert components are first prescreened to remove lumps and aggregates. A trilayered wafer is prepared by first blending the two components of Layer 1 into a uniform composition. 50 mg of this material is then added to the tablet die.

The three active ingredients in Layer 2 are blended and then further mixed with the glyceryl behenate and the polyethylene oxide excipients. This powder is then melted granulated by heating the powder blend to approximately 100° C. for six minutes.

The resulting mass is then cooled and milled by passing through a 60 mesh screen. 200 mg of this granulation is then added to the tablet die, followed by 100 mg of the granulated blended ingredients comprising Layer 3. The sides of the circular trilayered compressed wafer and the top lipophilic wax layer (Layer 3) are then coated with molten glyceryl behenate, leaving the bioadhesive layer (Layer 1) uncoated. The coated wafers are then heat treated at 72° C. for four minutes.

Method 16. A further embodiment of the present invention for the manufacture of a trilayered film comprises the following ingredients:

| Layer 1 | polyethylene oxide 4M | 20% |
|---|---|---|
| Layer 2 | epirubicin HCl | 8% |
| | lipase | 0.5% |
| | stearic acid | 14% |
| | glyceryl behenate | 49% |
| | pitavastatin | 3.5% |
| | poloxamer F68 | 10% |
| | polyethylene oxide 0.9M | 15% |
| Layer 3 | glyceryl behenate | 10% |

A film of polyethylene oxide is prepared by hot melt extrusion at processing temperatures in the extruder ranging from 75° C. to 140° C. To this film, a molten composition of Layer 2 is evenly spread and then cooled to room temperature. The glyceryl behenate in Layer 3 is melted and added onto the drug containing layer. The film is cooled and then cut into suitable sized wafers that are then heat cured at 68° C. for 4 hours.

Method 17: A further embodiment of the present invention provides for the manufacture of trilayered wafers comprised of the following composition:

| Layer 1 | polyethylene oxide 7M | 15 mg |
|---|---|---|
| Layer 2 | methotrexate | 10 mg |
| | dexamethasone sodium phosphate | 15 mg |
| | glyceryl behenate | 158 mg |
| | stearic acid | 14 mg |
| | polyethylene oxide 7M | 8 mg |
| Layer 3 | glyceryl behenate | 100 mg |

All inert components were passed through a 70 mesh screen. The trilayered wafer was prepared by first adding the polyethylene oxide 7M (Layer 1) to a tablet die. The powder blend containing the dexamethasone sodium phosphate and methotrexate was added to the glyceryl behenate and the stearic acid in the Layer 2 composition. The two lipids had previously been melt granulated by heating the powders of Layer 2 to 110° C. for five minutes. When this mass had been cooled and passed through a 60 mesh screen, the polyethylene oxide component of Layer 2 was then added to form the final powder blend for Layer 2, which was then incorporated into the trilayered wafer formulation. The melt granulated glyceryl behenate (Layer 3) was then added to the die, prior to compression into a trilayered wafer. The sides of the circular trilayered wafer and the top lipophilic wax layer (Layer 3) were then coated with molten glyceryl behenate at approximately 90° C., leaving the bioadhesive layer (Layer 1) uncoated and then cured at approximately 72° C. for ten minutes.

Method 18: A further embodiment of the present composition provides for the manufacture of trilayered wafers comprising carmustine as the active ingredient using the composition and method of preparation as described below.

| Layer 1 | polyethylene oxide 7M | 50 mg |
|---|---|---|
| Layer 2 | carmustine | 20 mg |
| | glyceryl behenate | 174 mg |
| | polyethylene oxide 7M | 6 mg |
| Layer 3 | Glyceryl behenate | 100 mg |

All inert components are passed through an 80 mesh screen. The trilayered wafer is prepared by first adding the polyethylene oxide 7M (Layer 1) to a tablet die. The powder blend containing the carmustine is added to the glyceryl behenate in the Layer 2 composition. The lipid is melt granulated by heating the powders of Layer 2 to 90° C. for two minutes. When this mass is cooled and passed through a 60 mesh screen, the polyethylene oxide component of Layer 2 is then added to form the final powder blend for Layer 2 and is added to the die. Then the melt granulated glyceryl behenate (Layer 3) is added to the die, prior to compression into a trilayered wafer. The sides of the circular trilayered wafer and the top lipophilic wax layer (Layer 3) were then coated with molten glyceryl behenate leaving the bioadhesive layer (Layer 1) uncoated and then cured at approximately 72° C. for ten minutes.

Method 19: A further embodiment of the present composition provides for the manufacture of trilayered wafers comprising doxorubicin as the active ingredient using the composition and method of preparation as described below.

| Layer 1 | polyethylene oxide 7M | 25 mg |
|---|---|---|
| Layer 2 | doxorubicin | 25 mg |
| | glyceryl behenate | 170 mg |
| | polyethylene oxide 7M | 5 mg |
| Layer 3 | Glyceryl behenate | 50 mg |

All inert components are passed through an 80 mesh screen. The trilayered wafer is prepared by first adding the polyethylene oxide 7M (Layer 1) to a tablet die. The powder blend containing the doxorubicin is added to the glyceryl behenate in the Layer 2 composition. The lipid and drug are melt granulated by heating the powders of Layer 2 to 90° C. for one minute. When this mass is cooled and passed through a 60 mesh screen, the polyethylene oxide component of Layer 2 is then added to form the final powder blend for Layer 2 and is added to the die. Then the melt granulated glyceryl behenate (Layer 3) is added to the die, prior to compression into a trilayered wafer. The sides of the circular trilayered wafer and the top lipophilic wax layer (Layer 3) are then coated with molten glyceryl behenate leaving the bioadhesive layer (Layer 1) uncoated and then cured at approximately 70° C. for fifteen minutes.

Method 20: A further embodiment of the present composition provides for the manufacture of trilayered wafers comprising topotecan as the active ingredient using the composition and method of preparation as described in Method 19.

| Layer 1 | polyethylene oxide 7M | 25 mg |
|---|---|---|
| Layer 2 | topotecan | 10 mg |
| | glyceryl behenate | 182 mg |
| | polyethylene oxide 7M | 8 mg |
| Layer 3 | Glyceryl behenate | 75 mg |

All inert components are passed through an 80 mesh screen. The trilayered wafer is prepared by first adding the polyethylene oxide 7M (Layer 1) to a tablet die. The powder blend containing the topotecan is added to the glyceryl behenate in the Layer 2 composition. The lipid and drug are melt granulated by heating the powders of Layer 2 to 90° C. for one minute. When this mass is cooled and passed through a 60 mesh screen, the polyethylene oxide component of Layer 2 is then added to form the final powder blend for Layer 2 and is added to the die. Then, melt granulated glyceryl behenate (Layer 3) is added to the die, prior to compression into a trilayered wafer. The sides of the circular trilayered wafer and the top lipophilic wax layer (Layer 3) are then coated with molten glyceryl behenate leaving the bioadhesive layer (Layer 1) uncoated and then cured at approximately 73° C. for ten minutes.

Method 21: A further embodiment of the present composition provides for the manufacture of trilayered wafers comprising D-actinomycin as the active ingredient using the composition and method of preparation as described in Method 19.

| Layer 1 | polyethylene oxide 7M | 35 mg |
|---|---|---|
| Layer 2 | D-actinomycin | 10 mg |
| | glyceryl behenate | 182 mg |
| | polyethylene oxide 7M | 7 mg |
| Layer 3 | Glyceryl behenate | 100 mg |

All inert components are passed through an 80 mesh screen. The trilayered wafer is prepared by first adding the polyethylene oxide 7M (Layer 1) to a tablet die. The powder blend containing the D-actinomycin is added to the glyceryl behenate in the Layer 2 composition. The lipid and drug are melt granulated by heating the powders of Layer 2 to 90° C. for one minute. When this mass is cooled and passed through a 60 mesh screen, the polyethylene oxide component of Layer 2 is then added to form the final powder blend for Layer 2 and is added to the die. Then, melt granulated glyceryl behenate (Layer 3) is added to the die, prior to compression into a trilayered wafer. The sides of the circular trilayered wafer and the top lipophilic wax layer (Layer 3) are then coated with molten glyceryl behenate leaving the bioadhesive layer (Layer 1) uncoated.

Method 22: A further embodiment of the present composition provides for the manufacture of trilayered wafers comprising a copper chelating agent such as D-penicillamine as the active ingredient using the composition and method of preparation as described in Method 19.

| Layer 1 | polyethylene oxide 7M | 50 mg |
|---|---|---|
| Layer 2 | D-penicillamine | 40 mg |
| | glyceryl behenate | 156 mg |
| | polyethylene oxide 1M | 4 mg |
| Layer 3 | Glyceryl behenate | 100 mg |

All inert components are passed through an 80 mesh screen. The trilayered wafer is prepared by first adding the polyethylene oxide 7M (Layer 1) to a tablet die. The powder blend containing the D-penicillamine is added to the glyceryl behenate in the Layer 2 composition. The lipid and drug are melt granulated by heating the powders of Layer 2 to 90° C. for one minute. When this mass is cooled and passed through a 60 mesh screen, the polyethylene oxide component of Layer 2 is then added to form the final powder blend for Layer 2 and is added to the die. Then, melt granulated glyceryl behenate (Layer 3) is added to the die, prior to compression into a trilayered wafer. The sides of the circular trilayered wafer and the top lipophilic wax layer (Layer 3) are then coated with molten glyceryl behenate leaving the bioadhesive layer (Layer 1) uncoated.

Method 23: A further embodiment of the present composition provides for the manufacture of trilayered wafers comprising a copper chelating agent such as D-penicillamine and paclitaxel as the active ingredient using the composition and method of preparation as described below.

| Layer 1 | polyethylene oxide 7M | 50 mg |
|---|---|---|
| Layer 2 | D-penicillamine | 30 mg |
| | Paclitaxel | 10 mg |
| | glyceryl behenate | 156 mg |
| | polyethylene oxide 1M | 4 mg |
| Layer 3 | Glyceryl behenate | 100 mg |

All inert components are passed through an 80 mesh screen. The trilayered wafer is prepared by first adding the polyethylene oxide 7M (Layer 1) to a tablet die. The powder blend containing the D-penicillamine and paclitaxel is added to the glyceryl behenate in the Layer 2 composition. The lipid and drugs are melt granulated by heating the powders of Layer 2 to 90° C. for one minute. When this mass is cooled and passed through a 60 mesh screen, the polyethylene oxide component of Layer 2 is then added to form the final powder blend for Layer 2 and is added to the die. Then, melt granulated glyceryl behenate (Layer 3) is added to the die, prior to compression into a trilayered wafer. The sides of the circular trilayered wafer and the top lipophilic wax layer (Layer 3) are then coated with molten glyceryl behenate leaving the bioadhesive layer (Layer 1) uncoated.

Method 24: A further embodiment of the present composition provides for the manufacture of trilayered wafers comprising a synthetic alkyl lysophospholipid such as edelfosine and paclitaxel as the active ingredients using the composition and method of preparation as described below.

| Layer 1 | polyethylene oxide 7M | 50 mg |
|---|---|---|
| Layer 2 | Edelfosine | 1 mg |
| | Paclitaxel | 10 mg |
| | glyceryl behenate | 182 mg |
| | polyethylene oxide 1M | 7 mg |
| Layer 3 | Glyceryl behenate | 100 mg |

All inert components are passed through an 80 mesh screen. The trilayered wafer is prepared by first adding the polyethylene oxide 7M (Layer 1) to a tablet die. The powder blend containing the edelfosine and paclitaxel is added to the glyceryl behenate in the Layer 2 composition. The lipid and drugs are melt granulated by heating the powders of Layer 2 to 90° C. for one minute. When this mass is cooled and passed through a 60 mesh screen, the polyethylene oxide component of Layer 2 is then added to form the final powder blend for Layer 2 and is added to the die. Then, melt granulated glyceryl behenate (Layer 3) is added to the die, prior to compression into a trilayered wafer. The sides of the circular trilayered wafer and the top lipophilic wax layer (Layer 3) are then coated with molten glyceryl behenate leaving the bioadhesive layer (Layer 1) uncoated.

Method 25: A further embodiment of the present composition provides for the manufacture of trilayered wafers comprising a bioactive sulfated saponin such as Sponin-1 (SAP-1) as the active ingredient using the composition and method of preparation as described below.

| Layer 1 | polyethylene oxide 7M | 50 mg |
| --- | --- | --- |
| Layer 2 | SAP-1 | 30 mg |
| | glyceryl behenate | 166 mg |
| | polyethylene oxide 1M | 4 mg |
| Layer 3 | Glyceryl behenate | 100 mg |

All inert components are passed through an 80 mesh screen. The trilayered wafer is prepared by first adding the polyethylene oxide 7M (Layer 1) to a tablet die. The powder blend containing SAP-1 is added to the glyceryl behenate in the Layer 2 composition. The lipid and drug are physically blended with the polyethylene oxide component of Layer 2 to form the final powder blend for Layer 2 and is added to the die. Then, melt granulated glyceryl behenate (Layer 3) is added to the die, prior to compression into a trilayered wafer. The sides of the circular trilayered wafer and the top lipophilic wax layer (Layer 3) are then coated with molten glyceryl behenate leaving the bioadhesive layer (Layer 1) uncoated.

Example 2

Generation of Multi-Layered Implants and Physiochemical Properties

Materials and Methods

Materials:

Acetaminophen, USP, was purchased from Spectrum Chemical (Gardena, Calif., USA). Compritol 888 ATO was generously provided by Gattefosse (Paramus, N.J., USA). Poly(ethylene oxide) was generously donated in three different grades (PolyOx N10, N12K, and 303) by Dow Chemical (Midland, Mich., USA). All other chemicals utilized in this study were of AC S grade.

Dispersion of Acetaminophen in Compritol®:

Acetaminophen and Compritol® were passed through a 70 mesh stainless steel screen prior to use. Homogenous blends of Compritol® and acetaminophen were prepared via geometric dilution using a mortar and pestle. The blend was placed for 5 minutes inside an oven set at 80° C. to melt Compritol®. Under constant mixing of a stirring rod, dispersion of acetaminophen in the molten Compritol® was poured onto an aluminum tray to allow Compritol® to solidify at ambient conditions. The solidified wax was ground up into small granules using a mortar and pestle. The granules were then passed through a 60 mesh stainless screen to obtain a dispersion of acetaminophen in Compritol®.

Preparation of Acetaminophen Wafers for Implant:

Three types of implant wafers, single layer, bilayer and tri-layer, were prepared in this study. As shown in FIG. 1, single layer wafer contained 200 mg drug layer only. Bilayer wafer was consisting of a 200 mg drug layer and 100 mg Compritol layer. In tri-layer wafer, 200 mg drug layer is sandwiched between 100 mg Compritol layer and 50 mg PolyOx layer.

An 11 mm in diameter, round and flat-faced tableting tooling was used to prepare the wafers. Powder blends for each individual layer were filled into die on a layer by layer fashion. The powder was compressed with a Carver press (Model MTCM-1, Globepharma, New Brunswick, N.J., US). The compression force was kept at 3000 psi.

Coating and Curing of Wafers for Implant:

Wafers were coated with a hydrophobic wax or polymer. Curing of wafers was performed using the column oven in a gas chromatography system (Agilent, Model GC 7820A, Santa Clara, Calif. US). The wafers were cured at 73° C. for a total of 10 minutes.

In Vitro Drug Release Testing:

Each implant was placed inside a 20 mL glass scintillation vial. Twenty milliliter 50 mM phosphate buffer pH 7.4 was added into each vial as the dissolution medium. The vials were stored inside an incubator chamber set at 37° C. Three milliliter dissolution medium was sampled at pre-determined time points. The buffer solution was used to replace the dissolution medium withdrawn at the time of sampling.

HPLC for the Quantitation of Acetaminophen in Dissolution Samples:

Dissolution samples were analyzed using a reversed phase HPLC method. Poroshell® 120, EC-C18, 2.7 µm, 4.6×50 mm (Agilent, Santa Clara, Calif., USA) was used as the HPLC column. A mixture of water and acetonitrile mixture (95:5 ratio) containing 0.05% trifluoroacetic acid was used as the mobile phase. The flow rate was set at 1.0 mL/min and the injection volume was 10 µL. A UV detector (Waters® 2998 PDA detector, Milford, Mass.) was used to quantitate at 275 nm. The retention time of acetaminophen was 2.1 minutes.

Differential Scanning Thermal Analysis:

Differential scanning calorimetry testing was performed using a TA Thermal Analyzer (Model DSC Q20, TA Instruments, New Castle, Del., US). The temperature was calibrated with an indium standard. Sample size was about 5 mg and a temperature ramp of 10° C. per minute was used. Universal Analysis 2000 data analysis software was used for data analysis. Inflection point method was used for the analysis of the glass transition temperature. The melting temperature is defined as the intersection of the extension of the baseline with the tangent at the inflection point of the curve.

Powder X-Ray Diffraction:

Powder X-ray diffraction (PXRD) was performed using a Rigaku Miniflex instrument (Rigaku, Woodlands, Tex., US). A Cu Kα ($\lambda$=1.54 Å) radiation with Ni filter, was used with a voltage of 40 kV, and a current of 100 mA. Samples of powder were placed into channeled stage and continuous scans were made from 10° to 40° 2θ with a step size of 0.05°.

Scanning Electron Microscopy:

Scanning electron microscopy (SEM) was performed according to established protocols.

Results from these experiments are shown in FIGS. 1-6. As shown in the figures drug release from the wafers was observed over a period of days. It is anticipated that this pharmacokinetic profile may be advantageously used to deliver a therapeutic compound to the brain.

As shown in FIG. 1, release of acetaminophen (APAP) from single layer (drug layer only) wafer was observed. Composition: 5% APAP, certain percent of PEO 303 (7,000,000 molar mass), and glycerol behenate q.s. to 100%, a total of 200 mg. Objective: to investigate the percent of PEO on drug release from drug layer only wafer. Conclusion: levels of PEO 303 between 1.5 and 4% were observed to be particularly effective.

Additional results are shown in FIGS. 2-6. A diagram of a multi-layered implant is shown in FIG. 7. Effect of the Molecular Weight and Percent of PolyOx on Drug Release from Coated Bilayer Wafer Implants was evaluated (N10, N12K and 303 at 0, 1.5 and 3.0%, w/w Lot 15-). Effect of the Molecular Weight and Percent of PolyOx on Drug Release from Coated Bilayer Wafer Implants (N10, N12K and 303 at 0, 4.0 and 5.0%, w/w Lot 16-) was evaluated. Effect of wax coating and bioadhesive layer on drug release from wafers (3% 303, 17-1: single layer; 17-3: coated bilayer; 17-5: coated tri-layer) was evaluated. Effect of curing was evaluated. Solubility of APAP in Compritol wax was evaluated.

Figure 6:
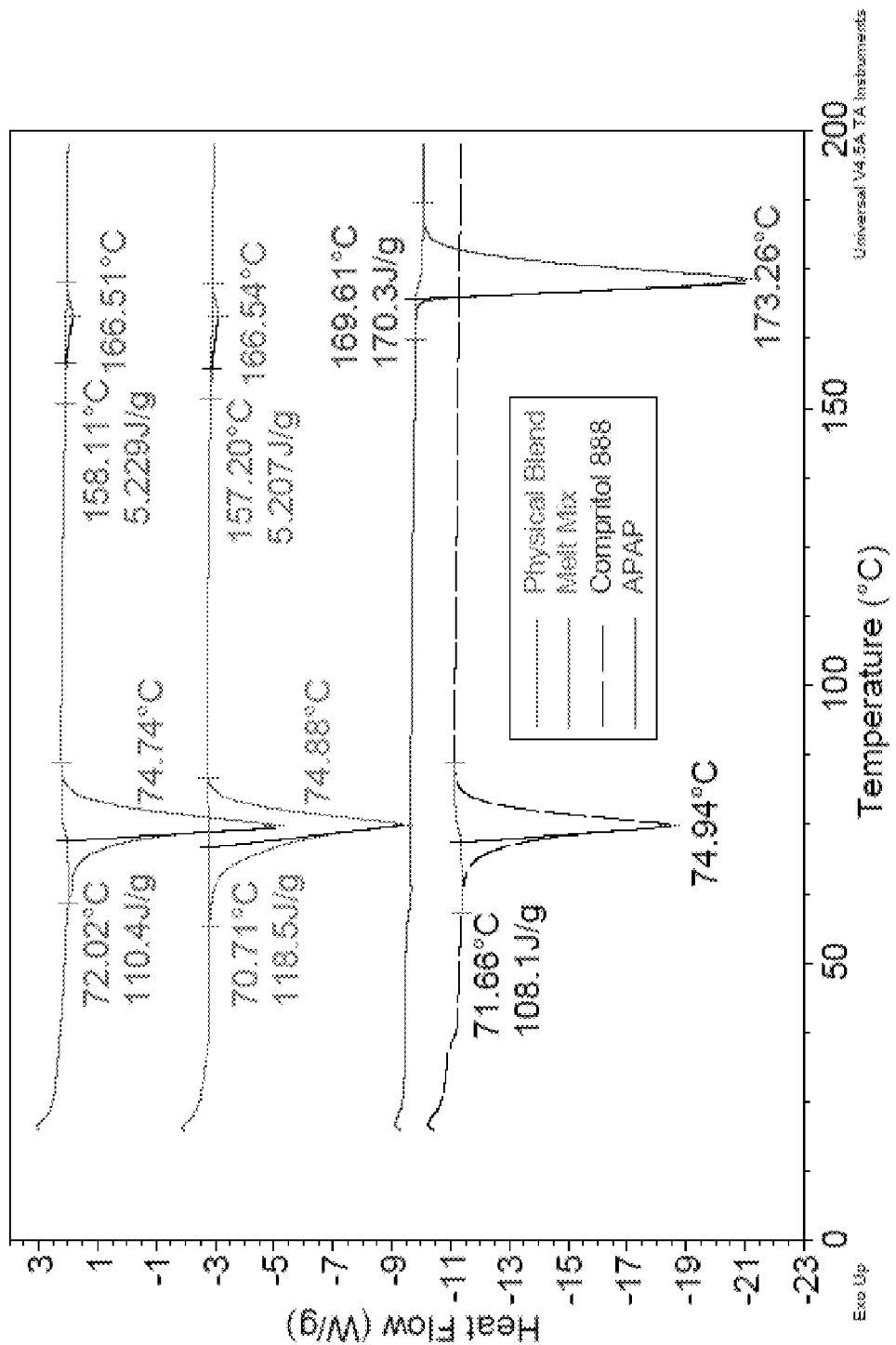
FIG. 6: DSC Thermogram of APAP, compritol, their mixture prepared by physical blending, and their mixture prepared using melt granulation.
Figure 7:
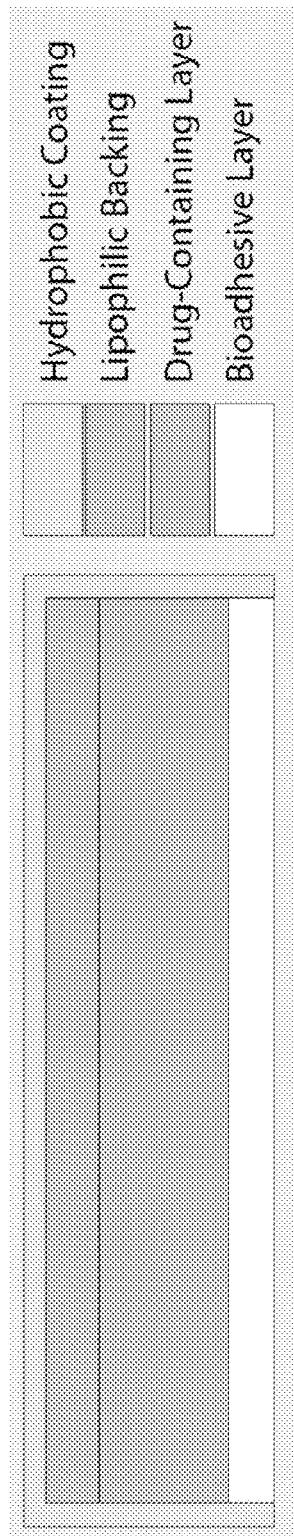
FIG. 7: An embodiment of a multi-layered wafer.

DSC results are shown in FIG. 6. Objective: analyze the physical state of APAP in glycerol behenate, Is APAP completed dissolved at molecular level or dispersed as crystalline particles? Conclusion: APAP is dispersed as crystalline particles. Physical blend: 5% APAP+95% glycerol behenate. Melt mix: 5% APAP+95% glycerol behenate processed using the melt granulation process. Compritol 888: glycerol behenate raw material, used as the reference. APAP: drug substance, used as the control.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 8,821,913 B2, "Controlled Releases System Containing Temozolomide", Y Wang, D. Fei, Sep. 2, 2014

D. Zhang, A. Tian. X. Xue, M. Wang, B. Qui, A. Wu, "The Effect of Temozolommide/Poly(lactide-co-glycolide) (PLGA)/Nano-Hydroxyapatite Microspheres on Glioma U87 Cells Behavior", *International Journal of Molecular Sciences*, 13(1), p 1109-1125, 2012.

U.S. Pat. No. 3,364,200, "Oxidized Cellulose Product and Method for Preparing the Same", W. Ashton, C. Moser, Jan. 16, 1968.

M. Aburahma, S. Badr-Eldin, "Compritol 888 ATO: A Multifactional Lipid Excipient in Drug Delivery Systems and Nanopharmaceuticals", *Expert Opinion on Drug Delivery*, 11(12), p 1865-1883, 2014.

F. Kreye, F. Siepmann, J. Siepmann, "Drug Release Mechanisms of Compressed Lipid Implants", *International Journal of Pharmaceutics*, 404(1-2), p 27-35, 2011.

K. Forier, K. Raemdonch, S. De Smedt, J. Demeester, T. coenye, K. Braeckmans, "Lipid and Polymer Nanoparticles for Drug Delivery to Bacterial Biofilms", *Journal of Controlled Release*, 190, p 607-623, 2014.

K. Cho, X. Wang, S. Nie, Z. Chen, D. Shin, "Therapeutic Nanoparticle for Drug Delivery in Cancer", Clinical Cancer Research, 14, p 1310, 2008.

S. Kalepu, M. Manthina. V. Padavala, "Oral Lipid-Based Drug Delivery Systems—An Overview", *Acta Pharmaceutica Sinica B*, 3(6), p 361-372, 2013.

S. Zara, M. Nabila, "Optimizing Oral Drug Delivery Using Lipid Based Formulations", *International Research Journal of Pharmacy*, 5(7), 2014.

M. Schwab, G. Sax, S. Schulze, G. Winter, "Studies on the Lipase Induced Degradation of Lipid Based Drug Delivery Systems", *Journal of Controlled Release*, 140, p 27-33, 2009.

F. Kreye, F. Siepmann, J. Siepmann, "Lipid Implants as Drug Delivery Systems", *Expert Opinion Drug Delivery*, 5(3), p 291-307, 2008.

L. Zhu, V. Kumar, G. Banker, "Examination of Aqueous Oxidized Cellulose Dispersions as a Potential Drug Carrier. I. Preparation and Characterization of Oxidized Cellulose-Phenylpropanolamine Complexes", *AAPS PharmSciTech*, 5(4), p 138-144, 2004.

U.S. Pat. No. 6,488,963 B1, J. McGinity and F. Zhang, "Hot-Melt Extrudable Pharmaceutical Formulation", Dec. 3, 2002.

M. Masserini, "Nanoparticles for Brain Drug Delivery", *International Scholarly Research Notices Biochemistry*, 2013, Article ID 238428, 2013.

P. Menei, C. Montero-Menei, M. C. Venier, J. P Benoit, "Drug Delivery into the Brain Using Poly(lactide-co-glycolide) Microspheres", *Expert Opinion Drug Delivery*, 2(2), 363-376, 2005.

C. Carbone, A. Campisi, T. Musumeci, G. Raciti, R. Bonfanti, G. Puglisi, "FA-Loaded Lipid Drug Delivery Systems: Preparation, Characterization and Biological Studies", *European Journal Pharmaceutical Sciences*, 14(52) p 12-20, 2014.

I. Shapira, D. Budman, T. Bradley, R. Gralla, "Evolving Lipid-Based Delivery Systems in the Management of Neoplastic Disease", *Oncology Reviews*, 113, 2009.

R. Upadhyay, "Drug Delivery Systems, CNS Protection, and the Blood Brain Barrier", *BioMed Research International*, 2014, Article ID 869269, 2014.

W. Pardridge, "Drug Delivery to the Brain", *Journal of Cerebral Blood Flow & Metabolism*, 17, p 713-731, 1997.

R. Gabathuler, "Approaches to Transport Therapeutic *Drugs Across the Blood-Brain Barrier to Treat Brain Diseases*", Neurobiology of Disease, 37, p 48-57, 2010.

G. Tiwari, R. Riwari, B. Sriwastawa, L. Bhati, S. Pandey, S. Bannerjee, "Drug Delivery Systems: An Updated Review, *International Journal of Pharmaceutical Investigation*, 2(1), p 2-11, 2012.

P. Jiang, R. Mukthavavam, Y. Chao, I. Bharati, V. Fogal, S. Pastorino, X. Cong, N. Nomura, M. Gallagher, T. Abbas, S. Vali, S. Pingle, M. Makale, S. Kesari, "Novel Antiglioblastoma Agents and Therapeutic Combinations Identified from a Collection of FDA Approved Drugs", *Journal of Translational Medicine,* 12, 2014.
U.S. Patent Publication No. 2004/0005647
U.S. Patent Publication No. 2006/0034925
U.S. Patent Publication No. 2006/0115537
U.S. Patent Publication No. 2006/0223114
U.S. Patent Publication No. 2006/0234299
U.S. Patent Publication No. 2007/0148095
U.S. Patent Publication No. 2012/0141550
U.S. Patent Publication No. 2013/0138032
U.S. Patent Publication No. 2014/0024610
U.S. Pat. No. 5,739,169
U.S. Pat. No. 5,801,005
U.S. Pat. No. 5,824,311
U.S. Pat. No. 5,830,880
U.S. Pat. No. 5,846,945
U.S. Pat. No. 6,232,287
U.S. Pat. No. 6,528,481
U.S. Pat. No. 7,452,964
U.S. Pat. No. 7,671,010
U.S. Pat. No. 7,781,565
U.S. Pat. No. 8,507,445
U.S. Pat. No. 8,450,278
PCT Publication No. 2008/121949
PCT Publication No. 2011/053435
PCT Publication No. 2014/087413
Anderson, N. G., *Practical Process Research & Development—A Guide For Organic Chemists,* $2^{nd}$ ed., Academic Press, New York, 2012.
Austin-Ward and Villaseca, *Rev. Med. Chil.,* 126(7):838-45, 1998.
Barclay et al. (eds.), The Leucocyte Antigen Facts Book, 1993, Academic Press.
Bukowski et al., *Clin. Cancer Res.,* 4(10):2337-47, 1998.
Burkly et al.: TWEAKing tissue remodeling by a multifunctional cytokine: role of TWEAK/Fn14 pathway in health and disease. *Cytokine* 40:1-16 (2007).
Campbell et al., *Cancer Res.,* 51(19):5329-5338 1991.
Christodoulides et al., *Microbiology,* 144(Pt 11):3027-37, 1998.
Davidson et al., *J. Immunother.,* 21(5):389-98, 1998.
Hanibuchi et al., *Int. J. Cancer,* 78(4):480-485, 1998.
Hellstrand et al., *Acta Oncol.,* 37(4):347-353, 1998.
Hui and Hashimoto, *Infect. Immun.,* 66(11):5329-36, 1998.
Ju et al., *Gene Ther.,* 7(19):1672-1679, 2000.
*March's Advanced Organic Chemistry: Reactions, Mechanisms, and Structure,* 2007.
Mitchell et al., *Ann. NY Acad. Sci.,* 690:153-166, 1993.
Mitchell et al., *J. Clin. Oncol.,* 8(5):856-869, 1990.
Morton et al., *Arch. Surg.,* 127:392-399, 1992.
Nechushtan et al., 1997
Onda et al., *Cancer Res.,* 64:1419-1424, 2004.
Pietras et al., *Oncogene,* 17(17):2235-49, 1998.
Qin et al., *Proc. Natl. Acad. Sci. USA,* 95(24):14411-14416, 1998.
Ravindranath and Morton, *Intern. Rev. Immunol.,* 7: 303-329, 1991.
Remington's Pharmaceutical Sciences, $15^{th}$ Ed., 1035-1038 and 1570-1580, 1990.
Remington's Pharmaceutical Sciences, $15^{th}$ Ed., 3:624-652, 1990.
Rosenberg et al., *Ann. Surg.* 210(4):474-548, 1989.
Rosenberg et al., *N. Engl. J. Med.,* 319:1676, 1988.
Thompson (ed.), 1994, *The Cytokine Handbook,* Academic Press, San Diego.
Weitman et al., *Cancer Res.,* 52(12):3396-3401, 1992b.
Weitman et al., *Cancer Res.,* 52(23):6708-6711, 1992a.
Winkles, *Nat Rev Drug Discov* 7:411-425 (2008).
Winthrop et al., *Clin. Cancer Res.,* 9:3845s-3853s, 2003.
Zhou, *Mol Cancer Ther.* 10(7):1276-88, 2011.

What is claimed is:

1. A biocompatible drug delivery implant for positioning adjacent to a biological tissue for delivering one or more drugs thereto, the implant comprising at least two layers, a drug-containing layer having a drug elution surface to be positioned proximal to the tissue, and, a further layer or layers comprising a lipophilic backing layer and/or a hydrophobic coating, said further layer or layers being positioned distal to the drug elution surface, wherein:
   a) the drug-containing layer comprises one or more drugs, a hydrophilic polymer or pore forming agent, and glyceryl behenate;
   b) the lipophilic backing layer comprises glyceryl behenate; and
   c) the hydrophobic coating comprises glyceryl behenate and coats surfaces of the implant that are not to be positioned proximal to the tissue and; and
   further, when each of layers a), b) and c) are present, the lipophilic backing layer is positioned between the drug-containing layer and the hydrophobic coating.

2. The implant of claim 1, wherein the implant further comprises a drug-permeable, hydrophilic layer d) positioned between the drug elution surface of the drug-containing layer and to be positioned proximal to the tissue.

3. The implant of claim 2, wherein the layer d) contains a steroid and the drug.

4. The implant of claim 3, wherein the steroid is dexamethasone.

5. The implant of claim 1, wherein the hydrophilic polymer present in layer a) and/or d) is a polyether or a polysaccharide.

6. The implant of claim 5, wherein the hydrophilic polymer is a polyethylene oxide, polypropylene oxide, or a polyethylene glycol.

7. The implant of claim 5, wherein the polysaccharide is chitosan or polyanhydroglucuronic acid.

8. The implant of claim 1, wherein the drug is an anti-cancer compound or a chemotherapeutic.

9. The implant of claim 8, wherein the chemotherapeutic is temozolomide, paclitaxel, cetuximab, irinotecan, everolimus, carboplatin, or docetaxel.

10. The implant of claim 1, wherein the implant is substantially circular or elliptical in shape or is further defined as a wafer.

11. The implant of claim 1, wherein the drug-containing layer comprises glyceryl behenate, stearic acid, polyanhydroglucuronic acid, or polyethylene oxide.

12. The implant of claim 1, wherein the hydrophobic coating further comprises stearic acid, palmitic acid, cholesterol, or chitosan.

13. The implant of claim 1, wherein the drug-containing layer further comprises stearic acid, lipase, cholesterol, glyceryl tristearate, poloxamer F-68, and/or polyanhydroglucuronic acid.

14. The implant of claim 1, wherein the implant comprises: 0.1-50% of the drug, 5-95% of glyceryl behenate, and about 3-50% of the hydrophilic polymer or pore forming agent.

15. The implant of claim 1, comprising layers a) and b).

16. The implant of claim 1, comprising layers a) and c).

17. The implant of claim 1, comprising layers a), b) and c).

18. The implant of claim 2, wherein the layer d) does not contain the drug.

19. The implant of claim 2, wherein the layer d) contains a steroid.

20. The implant of claim 2, wherein the layer d) contains the drug.

21. The implant of claim 6, wherein the hydrophilic polymer is a polyethylene oxide.

22. The implant of claim 5, wherein the hydrophilic polymer is a polysaccharide.

23. The implant of claim 5, wherein the hydrophilic polymer comprises a mixture of a polyether and a polysaccharide.

24. The implant of claim 23, wherein the hydrophilic polymer is a mixture comprising polyethylene oxide and chitosan.

25. The implant of claim 5, wherein the hydrophilic polymer is polyethylene oxide or polyanhydroglucuronic acid.

26. The implant of claim 5, wherein the hydrophilic polymer is polyethylene oxide, chitosan, povidone (PVP or polyvinylpyrrolidone), or polyanhydroglucuronic acid.

27. The implant of claim 8, wherein the anti-cancer compound is a chemotherapy or a chemotherapeutic agent.

28. The implant of claim 1, wherein the drug is cisplatin, topotecan, bevacizumab, doxorubicin, everolimus, paclitaxel, irinotecan, carboplatin, D-actinomycin, docetaxel, pitavastatin, methotrexate, temozolomide, epirubicin, cetuximab, a copper chelating agent, carmustine, a synthetic alkyl lysophospholipid, a bioactive sulfated saponin, steroid, or a statin.

29. The implant of any one of claim 1, wherein the drug is a steroid.

30. The implant of any one of claim 1, wherein layer a) comprises both a chemotherapeutic agent and a steroid.

31. The implant of claim 2, wherein layer a) comprises a chemotherapeutic agent, and wherein the implant further comprises the layer d), wherein layer d) comprises a steroid.

32. The implant of claim 31, wherein layer a) further comprises a steroid.

33. The implant of any one of claim 29, wherein the steroid is dexamethasone or dexamethasone sodium phosphate.

34. The implant of claim 30, wherein chemotherapeutic agent is temozolomide or paclitaxel; and wherein the steroid is dexamethasone.

35. The implant of any one of claim 1, wherein the implant is further defined as a wafer.

36. The implant of claim 35, wherein the wafer or tablet is configured for insertion into a resection cavity.

37. The implant of claim 1, wherein the implant or wafer further comprises an additional therapeutic agent.

38. The implant of claim 37, wherein the additional therapeutic agent is an antibiotic, an antimicrobial agent, a statin, an anti-fungal agent, an anti-viral agent, a steroid, an anesthetic, a local anesthetic, or a NSAID.

39. The implant of claim 38, wherein the additional therapeutic agent is an antibiotic or an antimicrobial agent.

40. The implant of claim 1, wherein the implant does not contain an organic solvent.

41. The implant of claim 1, wherein the implant contains an organic solvent.

42. The implant of claim 41, wherein the implant contains no more than a trace amount or a residual amount of the organic solvent.

43. The implant of claim 41, wherein the organic solvent is ethanol, dichloromethane, acetone, tetrahydrofuran, or ethyl acetate.

44. The implant of claim 1, wherein the lipophilic backing layer and the hydrophobic coating are made of the same or essentially the same compounds or mixture of compounds.

45. The implant of claim 44, wherein the lipophilic backing layer and the hydrophobic coating together form a substantially homogenous hydrophobic layer.

46. The implant of claim 1, wherein the lipophilic backing layer and the hydrophobic coating comprise different compounds.

47. The implant of claim 1, wherein the hydrophobic coating consists of or consists essentially of glyceryl behenate.

48. The implant of claim 1, where the drug-containing layer comprises glyceryl behenate and stearic acid, in combination with polyanhydroglucuronic acid and/or polyethylene oxide.

49. The implant of claim 48, wherein the drug-containing layer comprises glyceryl behenate, stearic acid, and polyethylene oxide.

50. The implant of claim 48, wherein the drug-containing layer further comprises lipase, cholesterol, glyceryl tristearate, and/or poloxamer F-68.

51. The implant of claim 50, wherein layer c) and/or layer b) contain lipase.

52. The implant of claim 1, wherein the drug-containing layer comprises polyethylene oxide or polyanhydroglucoronic acid.

53. The implant of claim 52, wherein the drug-containing layer comprises polyethylene oxide, glycerol behenate, and/or cholesterol.

54. The implant of claim 1, wherein the hydrophilic polymer is a polyethylene oxide, a polysaccharide, a protein, an oxidized cellulose polymer, polyanhydroglucuronic acid, a poloxomer, chitosan, or providone (PVP).

55. The implant of claim 1, wherein the implant further comprises lipase.

56. The implant of claim 1, wherein the implant is configured for insertion into a resection cavity.

57. The implant of claim 1, wherein the implant has been cured at temperatures of at least about 40° C., 45° C., 50° C., 55° C., 60° C., 65° C., 70° C., 75° C., 80° C., 85° C., 90° C., 95° C., 100° C., or up to 200° C.

58. The implant of claim 1, wherein the implant has been sterilized by gamma radiation, ethylene oxide, or electron beam radiation.

59. The implant of claim 1, wherein the implant or wafer has been processed by compression, hot-melt extrusion, injection molding, dry powder coating, dipping, coating, spraying, hot-melt granulation, casting, an evaporation technology, or any combination thereof.

60. The implant of claim 1, wherein the implant is further defined as a bilayered implant or wafer.

61. The implant of claim 1, wherein the implant is further defined as a trilayered implant or wafer.

62. The implant of claim 1, wherein the implant allows for release of the drug over a period of at least 3, 4, 5, 6, 7, 8, 9, 10, 11, 12, 13, 14, 15, 16, 17, 18, 19, 20, 21, 22, 23, 24, 25, 26, 27, 28, 29, or 30 or more days, or at least 1, 2, 3, 4, 5, or 6 weeks, or any range derivable therein.

63. The implant of claim 1, wherein the implant further comprises a surfactant, a carbohydrate, a polyol, a protein, a peptide, and/or an excipient.

64. A method of treating a disease or traumatic injury in a mammalian subject, comprising administering into a resection cavity in the subject the implant of claim 1, wherein the drug elution surface is positioned proximal to the resection cavity, and, the further layer or layers comprising the lipophilic backing layer and/or the hydrophobic coating are positioned distal and/or lateral to the drug elution surface.

* * * * *